United States Patent
Minor et al.

(10) Patent No.: US 7,479,239 B2
(45) Date of Patent: Jan. 20, 2009

(54) 1,1,1,2,2,4,5,5,5-NONAFLUORO-4-(TRIFLUOROMETHYL)-3-PENTANONE COMPOSITIONS COMPRISING A HYDROFLUOROCARBON AND USES THEREOF

(75) Inventors: Barbara Haviland Minor, Elkton, MD (US); Mario Joseph Nappa, Newark, DE (US); Allen Capron Sievert, Elkton, MD (US); Thomas J. Leck, Hockessin, DE (US)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/939,201

(22) Filed: Nov. 13, 2007

(65) Prior Publication Data

US 2008/0061265 A1 Mar. 13, 2008

Related U.S. Application Data

(62) Division of application No. 11/437,024, filed on May 19, 2006, now Pat. No. 7,314,576, which is a division of application No. 11/063,203, filed on Feb. 22, 2005, now Pat. No. 7,153,448.

(60) Provisional application No. 60/575,037, filed on May 26, 2004, provisional application No. 60/584,785, filed on Jun. 29, 2004.

(51) Int. Cl.
 *C09K 5/04* (2006.01)
(52) U.S. Cl. .......................................... 252/68; 252/67
(58) Field of Classification Search ................... 252/67, 252/68
See application file for complete search history.

(56) References Cited

U.S. PATENT DOCUMENTS

| 5,037,573 | A | 8/1991 | Merchant |
| 5,039,445 | A | 8/1991 | Merchant |
| 5,302,212 | A | 4/1994 | Desboemdrs et al. |
| 6,299,792 | B1 | 10/2001 | Feiring et al. |
| 6,423,673 | B1 | 7/2002 | Owens et al. |
| 2004/0226303 | A1 | 11/2004 | Jannick et al. |
| 2005/0166607 | A1 | 8/2005 | Brasz et al. |

FOREIGN PATENT DOCUMENTS

| EP | 520860 | | 12/1992 |
| JP | 2002226839 | | 8/2002 |
| WO | WO 96/40834 | * | 12/1996 |
| WO | WO 97/31989 | | 9/1997 |
| WO | WO 02/052072 | | 7/2002 |
| WO | WO 03/018707 A1 | | 3/2003 |

OTHER PUBLICATIONS

Biancardi et. al., "Component Design Issues and Limitations With 3$^{rd}$ Generation HFC, HC and Natural Refrigerants", Science et Technique du Froid, 1994, pp. 365-386.
International Search Report, date of mailing: Aug. 29, 2006.
Written Opinion of the International Search Authority, date of mailing: Aug. 29, 2006.

* cited by examiner

*Primary Examiner*—John R Hardee
(74) *Attorney, Agent, or Firm*—Jane O. Hamby

(57) ABSTRACT

Disclosed herein are refrigerant and heat transfer fluid compositions comprising 1,1,1,2,2,4,5,5,5-nonafluoro-4-(trifluoromethyl)-3-pentanone and at least one hydrofluorocarbon for use in refrigeration and air conditioning systems employing a centrifugal compressor. The compositions may be azeotropic or near-azeotropic.

16 Claims, No Drawings

1,1,1,2,2,4,5,5,5-NONAFLUORO-4-(TRIFLUOROMETHYL)-3-PENTANONE COMPOSITIONS COMPRISING A HYDROFLUOROCARBON AND USES THEREOF

CROSS REFERENCE(S) TO RELATED APPLICATION(S)

This application is a divisional application of Ser. No. 11/437,024 issued U.S. Pat. No. 7,314,576, filed May 19, 2006, which is a divisional of Ser. No. 11/063,203 issued U.S. Pat. No. 7,153,448 filed Feb. 22, 2005, which claims the priority benefit of U.S. Provisional Application 60/575,037, filed May 26, 2004, and U.S. Provisional Application 60/584, 785, filed Jun. 29, 2004.

BACKGROUND OF THE INVENTION

1. Field of the Invention

The present invention relates to compositions for use in refrigeration and air conditioning systems comprising at least one hydrofluorocarbon and 1,1,1,2,2,4,5,5,5-nonafluoro-4-(trifluoromethyl)-3-pentanone (PEIK). Further, the present invention relates to compositions for use in refrigeration and air-conditioning systems employing a centrifugal compressor comprising at least one hydrofluorocarbon and 1,1,1,2,2,4,5, 5,5-nonafluoro-4-(trifluoromethyl)-3-pentanone. The compositions of the present invention may be azeotropic or near azeotropic and are useful in processes for producing refrigeration or heat or as heat transfer fluids.

2. Description of Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, HFC-134a being the most widely used at this time, have zero ozone depletion potential and thus are not affected by the current regulatory phase out as a result of the Montreal Protocol.

Further environmental regulations may ultimately cause global phase out of certain HFC refrigerants as well. Currently, the automobile industry is facing regulations relating to global warming potential for refrigerants used in mobile air-conditioning. Therefore, there is a great current need to identify new refrigerants with reduced global warming potential for the automobile air-conditioning market. Should the regulations be more broadly applied in the future, an even greater need will be felt for refrigerants that can be used in all areas of the refrigeration and air-conditioning industry.

Currently proposed replacement refrigerants for HFC-134a include HFC-152a, pure hydrocarbons such as butane or propane, or "natural" refrigerants such as $CO_2$ or ammonia. Many of these suggested replacements are toxic, flammable, and/or have low energy efficiency. Therefore, new alternatives are constantly being sought.

The object of the present invention is to provide novel refrigerant compositions and heat transfer fluids that provide unique characteristics to meet the demands of low or zero ozone depletion potential and lower global warming potential as compared to current refrigerants.

BRIEF SUMMARY OF THE INVENTION

The present invention relates to compositions comprising:
1,1,1,2,2,4,5,5,5-nonafluoro-4-(trifluoromethyl)-3-pentanone and 1,1,3-trifluoropropane;
1,1,1,2,2,4,5,5,5-nonafluoro-4-(trifluoromethyl)-3-pentanone and 1,3-difluoropropane;
1,1,1,2,2,4,5,5,5-nonafluoro-4-(trifluoromethyl)-3-pentanone and 1,1,1,3,3-pentafluorobutane;
1,1,1,2,2,4,5,5,5-nonafluoro-4-(trifluoromethyl)-3-pentanone and 1,1-difluorobutane;
1,1,1,2,2,4,5,5,5-nonafluoro-4-(trifluoromethyl)-3-pentanone and 1,2-difluorobutane;
1,1,1,2,2,4,5,5,5-nonafluoro-4-(trifluoromethyl)-3-pentanone and 1,3-difluorobutane;
1,1,1,2,2,4,5,5,5-nonafluoro-4-(trifluoromethyl)-3-pentanone and 1,4-difluorobutane;
1,1,1,2,2,4,5,5,5-nonafluoro-4-(trifluoromethyl)-3-pentanone and 1,3-difluoro-2-methylpropane;
1,1,1,2,2,4,5,5,5-nonafluoro-4-(trifluoromethyl)-3-pentanone and 1,2-difluoro-2-methylpropane;
1,1,1,2,2,4,5,5,5-nonafluoro-4-(trifluoromethyl)-3-pentanone and 2,3-difluorobutane;
1,1,1,2,2,4,5,5,5-nonafluoro-4-(trifluoromethyl)-3-pentanone and 1,1,1-trifluoropentane;
1,1,1,2,2,4,5,5,5-nonafluoro-4-(trifluoromethyl)-3-pentanone and 1,1,1-trifluoro-3-methylbutane;
1,1,1,2,2,4,5,5,5-nonafluoro-4-(trifluoromethyl)-3-pentanone and 1,1-difluoropentane;
1,1,1,2,2,4,5,5,5-nonafluoro-4-(trifluoromethyl)-3-pentanone and 1,2-difluoropentane;
1,1,1,2,2,4,5,5,5-nonafluoro-4-(trifluoromethyl)-3-pentanone and 2,2-difluoropentane;
1,1,1,2,2,4,5,5,5-nonafluoro-4-(trifluoromethyl)-3-pentanone and 1,1,1,2,2,3,4,5,5,5-decafluoropentane;
1,1,1,2,2,4,5,5,5-nonafluoro-4-(trifluoromethyl)-3-pentanone and 1,1,1-trifluorohexane;
1,1,1,2,2,4,5,5,5-nonafluoro-4-(trifluoromethyl)-3-pentanone and 1,1,2,2-tetrafluorocyclobutane; and The present invention further relates to the above listed compositions specifically for use in refrigeration or air conditioning systems employing a centrifugal compressor.

The present invention further relates to the above listed compositions specifically for use in refrigeration or air conditioning systems employing a multi-stage or 2-stage centrifugal compressor.

The present invention further relates to the above listed compositions specifically for use in refrigeration or air conditioning systems employing a single pass/single slab heat exchanger.

The present invention further relates to azeotropic or near azeotropic refrigerant compositions. These compositions are useful in refrigeration or air conditioning systems. The compositions are also useful in refrigeration or air conditioning systems employing a centrifugal compressor.

The present invention further relates to processes for producing refrigeration, heat, and transfer of heat from a heat source to a heat sink using the present inventive compositions.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The refrigerant compositions of the present invention comprise 1,1,1,2,2,4,5,5,5-nonafluoro-4-(trifluoromethyl)-3-pentanone (PEIK) and a hydrofluorocarbon (HFC). The compositions of the present invention may comprise mixtures of more than one HFC, wherein these mixtures are then combined with 1,1,1,2,2,4,5,5,5-nonafluoro-4-(trifluoromethyl)-3-pentanone (PEIK).

The hydrofluorocarbons of the present invention comprise compounds containing hydrogen, fluorine and carbon. These hydrofluorocarbons may be represented by the formula $C_xH_{2x+2-y}F_y$ or $C_xH_{2x-y}F_y$. In the formulas, x may equal 3 to 8 and y may equal 1-17. The hydrofluorocarbons may be straight chain, branched chain or cyclic; saturated or unsaturated compounds having from about 3 to 8 carbon atoms. Representative hydrofluorocarbons are listed in Table 1.

TABLE 1

| Compound | Chemical Formula | Chemical Name | CAS Reg. No. |
|---|---|---|---|
| Hydrofluorocarbons | | | |
| HFC-245ca | $CHF_2CF_2CH_2F$ | 1,1,2,2,3-pentafluoropropane | 679-86-7 |
| HFC-245fa | $CF_3CH_2CHF_2$ | 1,1,1,3,3-pentafluoropropane | 460-73-1 |
| HFC-263fa | $CHF_2CH_2CH_2F$ | 1,1,3-trifluoropropane | 24270-67-5 |
| HFC-272fa | $CH_2FCH_2CH_2F$ | 1,3-difluoropropane | 462-39-5 |
| HFC-338mpy | $CHF_2CF(CF_3)CHF_2$ | 2-(difluoromethyl)-1,1,1,2,3,3-hexafluoropropane | 65781-21-7 |
| HFC-338pcc | $CHF_2CF_2CF_2CHF_2$ | 1,1,2,2,3,3,4,4-octafluorobutane | 377-36-6 |
| HFC-356mcf | $CF_3CF_2CH_2CH_2F$ | 1,1,1,2,2,4-hexafluorobutane | 161791-33-9 |
| HFC-365mfc | $CF_3CH_2CF_2CH_3$ | 1,1,1,3,3-pentafluorobutane | 406-58-6 |
| HFC-392p | $CF_2HCH_2CH_2CH_3$ | 1,1-difluorobutane | 2358-38-5 |
| HFC-392qqz | $(CH_2F)_2CHCH_3$ | 1,3-difluoro-2-methylpropane | 62126-93-6 |
| HFC-392qy | $CH_2FCF(CH_3)_2$ | 1,2-difluoro-2-methylpropane | 62126-92-5 |
| HFC-392qe | $CH_2FCHFCH_2CH_3$ | 1,2-difluorobutane | 686-65-7 |
| HFC-392qfe | $CH_2FCH_2CHFCH_3$ | 1,3-difluorobutane | 691-42-9 |
| HFC-392qff | $CH_2FCH_2CH_2CH_2F$ | 1,4-difluorobutane | 372-90-7 |
| HFC-392see | $CH_3CHFCHFCH_3$ | 2,3-difluorobutane | 666-21-7 |
| HFC-42-11mmyc | $(CF_3)_2CFCF_2CHF_2$ | 1,1,1,2,3,3,4,4-octafluoro-2-(trifluoromethyl)butane | 1960-20-9 |
| HFC-42-11p | $CHF_2CF_2CF_2CF_2CF_3$ | 1,1,1,2,2,3,3,4,4,5,5-undecafluoropentane | 375-61-1 |
| HFC-43-10mee | $CF_3CHFCHFCF_2CF_3$ | 1,1,1,2,2,3,4,5,5,5-decafluoropentane | 138495-42-8 |
| HFC-43-10mf | $CF_3CH_2CF_2CF_2CF_3$ | 1,1,1,2,2,3,3,5,5,5-decafluoropentane | 755-45-3 |
| HFC-449mmzf | $(CF_3)_2CHCH_2CF_3$ | 1,1,1,4,4,4-hexafluoro-2-(trifluoromethyl)butane | 367-53-3 |
| HFC-4-10-3m | $CF_3(CH_2)_3CH_3$ | 1,1,1-trifluoropentane | 402-82-6 |
| HFC-4-10-3mfsz | $CF_3CH_2CH(CH_3)_2$ | 1,1,1-trifluoro-3-methylbutane | 406-49-5 |
| HFC-4-11-2p | $CHF_2(CH_2)_3CH_3$ | 1,1-difluoropentane | 62127-40-6 |
| HFC-4-11-2qe | $CH_2FCHF(CH_2)_2CH_3$ | 1,2-difluoropentane | 62126-94-7 |
| HFC-4-11-2sc | $CH_3CF_2CH_2CH_2CH_3$ | 2,2-difluoropentane | 371-65-3 |
| HFC-5-12-3m | $CF_3(CH_2)_4CH_3$ | 1,1,1-trifluorohexane | 17337-12-1 |
| HFC-52-13p | $CHF_2CF_2CF_2CF_2CF_2CF_3$ | 1,1,1,2,2,3,3,4,4,5,5,6,6-tridecafluorohexane | 355-37-3 |
| HFC-54-11mmzf | $(CF_3)_2CHCH_2CF_2CF_3$ | 1,1,1,2,2,5,5,5-octafluoro-4-(trifluoromethyl)pentane | 90278-01-6 |
| HFC-C354cc | $c\text{-}CF_2CF_2CH_2CH_2\text{—}$ | 1,1,2,2,-tetrafluorocyclobutane | 374-12-9 |
| PFBE | $CF_3(CF_2)_3CH{=}CH_2$ | 3,3,4,4,5,5,6,6-nonafluoro-1-hexene (or perfluorobutylethylene) | 19430-93-4 |
| Fluoroketone | | | |
| PEIK | $CF_3CF_2C(O)CF(CF_3)_2$ | 1,1,1,2,2,4,5,5,5-nonafluoro-4-(trifluoromethyl)-3-pentanone (or perfluoroethylisopropyl ketone) | 756-13-8 |

The compounds listed in Table 1 are available commercially or may be prepared by processes known in the prior art. 1,1,1,2,2,4,5,5,5-nonafluoro-4-(trifluoromethyl)-3-pentanone (PEIK) is commercially available from 3M™ (St. Paul, Minn.).

Compositions of the present invention have low or zero ozone depletion potential and low global warming potential. For example, lightly fluorinated hydrofluorocarbons and PEIK, alone or in mixtures will have global warming potentials lower than many HFC refrigerants currently in use.

The compositions of the present invention may be prepared by any convenient method to combine the desired amounts of the individual components. A preferred method is to weigh the desired component amounts and thereafter combine the components in an appropriate vessel. Agitation may be used, if desired.

The refrigerant compositions of the present invention include the following:

1,1,1,2,2,4,5,5,5-nonafluoro-4-(trifluoromethyl)-3-pentanone and 1,1,3-trifluoropropane;
1,1,1,2,2,4,5,5,5-nonafluoro-4-(trifluoromethyl)-3-pentanone and 1,3-difluoropropane;
1,1,1,2,2,4,5,5,5-nonafluoro-4-(trifluoromethyl)-3-pentanone and 1,1,1,3,3-pentafluorobutane;
1,1,1,2,2,4,5,5,5-nonafluoro-4-(trifluoromethyl)-3-pentanone and 1,1-difluorobutane;
1,1,1,2,2,4,5,5,5-nonafluoro-4-(trifluoromethyl)-3-pentanone and 1,2-difluorobutane;
1,1,1,2,2,4,5,5,5-nonafluoro-4-(trifluoromethyl)-3-pentanone and 1,3-difluorobutane;
1,1,1,2,2,4,5,5,5-nonafluoro-4-(trifluoromethyl)-3-pentanone and 1,4-difluorobutane;
1,1,1,2,2,4,5,5,5-nonafluoro-4-(trifluoromethyl)-3-pentanone and 1,3-difluoro-2-methylpropane;
1,1,1,2,2,4,5,5,5-nonafluoro-4-(trifluoromethyl)-3-pentanone and 1,2-difluoro-2-methylpropane;
1,1,1,2,2,4,5,5,5-nonafluoro-4-(trifluoromethyl)-3-pentanone and 2,3-difluorobutane;
1,1,1,2,2,4,5,5,5-nonafluoro-4-(trifluoromethyl)-3-pentanone and 1,1,1-trifluoropentane;
1,1,1,2,2,4,5,5,5-nonafluoro-4-(trifluoromethyl)-3-pentanone and 1,1,1-trifluoro-3-methylbutane;
1,1,1,2,2,4,5,5,5-nonafluoro-4-(trifluoromethyl)-3-pentanone and 1,1-difluoropentane;
1,1,1,2,2,4,5,5,5-nonafluoro-4-(trifluoromethyl)-3-pentanone and 1,2-difluoropentane;
1,1,1,2,2,4,5,5,5-nonafluoro-4-(trifluoromethyl)-3-pentanone and 2,2-difluoropentane;
1,1,1,2,2,4,5,5,5-nonafluoro-4-(trifluoromethyl)-3-pentanone and 1,1,1,2,2,3,4,5,5,5-decafluoropentane;
1,1,1,2,2,4,5,5,5-nonafluoro-4-(trifluoromethyl)-3-pentanone and 1,1,1-trifluorohexane;
1,1,1,2,2,4,5,5,5-nonafluoro-4-(trifluoromethyl)-3-pentanone and 1,1,2,2-tetrafluorocyclobutane; and
1,1,1,2,2,4,5,5,5-nonafluoro-4-(trifluoromethyl)-3-pentanone and 3,3,4,4,5,5,6,6,6-nonafluoro-1-hexene.

The refrigerant or heat transfer compositions of the present invention may be azeotropic or near azeotropic compositions. An azeotropic composition is a liquid admixture of two or more substances that has a constant boiling point that may be above or below the boiling points of the individual components. As such an azeotropic composition will not fractionate within the refrigeration or air conditioning system during operation, which may reduce efficiency of the system. Additionally, an azeotropic composition will not fractionate upon leakage from the refrigeration or air conditioning system. In the situation where one component of a mixture is flammable, fractionation during leakage could lead to a flammable composition either within the system or outside of the system.

A near azeotropic composition is a substantially constant boiling, liquid admixture of two or more substances that behaves essentially as a single substance. One way to characterize a near azeotropic composition is that the vapor produced by partial evaporation or distillation of the liquid has substantially the same composition as the liquid from which it was evaporated or distilled, that is, the admixture distills/refluxes without substantial composition change. Another way to characterize a near azeotropic composition is that the bubble point vapor pressure and the dew point vapor pressure of the composition at a particular temperature are substantially the same. Herein, a composition is near azeotropic if, after 50 weight percent of the composition is removed, such as by evaporation or boiling off, the difference in vapor pressure between the original composition and the composition remaining after 50 weight percent of the original composition has been removed is less than about 10 percent.

The azeotropic refrigerant compositions of the present invention are listed in Table 2.

TABLE 2

| Component A | Component B | Azeotrope Concentration Wt % A | Wt % B | Azeotrope BP (° C.) |
|---|---|---|---|---|
| PEIK | HFC-263fa | 78.4 | 21.6 | 46.0 |
| PEIK | HFC-272fa | 74.7 | 25.3 | 33.5 |
| PEIK | HFC-392p | 50.6 | 49.4 | 37.6 |
| PEIK | HFC-392qe | 78.4 | 21.6 | 37.2 |
| PEIK | HFC-392qfe | 84.9 | 15.1 | 41.3 |
| PEIK | HFC-392qff | 92.5 | 7.5 | 45.8 |
| PEIK | HFC-392qqz | 86.8 | 13.2 | 41.7 |
| PEIK | HFC-392qy | 55.9 | 44.1 | 31.5 |
| PEIK | HFC-392see | 75.0 | 25.0 | 36.0 |
| PEIK | HFC-4-10-3m | 47.5 | 52.5 | 36.2 |
| PEIK | HFC-4-10-3mfsz | 45.4 | 54.6 | 35.4 |
| PEIK | HFC-4-11-2p | 95.2 | 4.8 | 48.7 |
| PEIK | HFC-4-11-2qe | 90.1 | 9.9 | 44.8 |
| PEIK | HFC-4-11-2sc | 82.0 | 18.0 | 45.2 |
| PEIK | HFC-43-10mee | 73.6 | 26.4 | 46.0 |
| PEIK | HFC-5-12-3m | 96.0 | 4.0 | 48.8 |
| PEIK | HFC-C354cc | 73.2 | 26.8 | 48.7 |

The near azeotropic refrigerant compositions and concentration ranges of the present invention are listed in Table 3.

TABLE 3

| Compounds (A/B) | Near Azeotropic Concentration Range wt % A/wt % B |
|---|---|
| PEIK/HFC-263fa | 1-99/99-1 |
| PEIK/HFC-272fa | 1-90/99-10 |
| PEIK/HFC-365mfc | 1-99/99-1 |
| PEIK/HFC-392p | 1-99/99-1 |
| PEIK/HFC-392qe | 54-91/46-9 |
| PEIK/HFC-392qfe | 65-95/35-5 |
| PEIK/HFC-392qff | 76-99/24-1 |
| PEIK/HFC-392qqz | 68-95/32-5 |
| PEIK/HFC-392qy | 1-84/99-16 |
| PEIK/HFC-392see | 48-90/52-10 |
| PEIK/HFC-4-10-3m | 1-86/99-14 |
| PEIK/HFC-4-10-3mfsz | 1-84/99-16 |
| PEIK/HFC-4-11-2p | 62-99/38-1 |
| PEIK/HFC-4-11-2qe | 72-99/28-1 |
| PEIK/HFC-4-11-2sc | 51-99/49-1 |
| PEIK/HFC-43-10mee | 1-99/99-1 |
| PEIK/HFC-5-12-3m | 65-99/35-1 |
| PEIK/HFC-C354cc | 1-99/99-1 |
| PEIK/PFBE | 1-99/99-1 |

The compositions of the present invention may further comprise about 0.01 weight percent to about 5 weight percent of a stabilizer, free radical scavenger or antioxidant. Such additives include but are not limited to, nitromethane, hindered phenols, hydroxylamines, thiols, phosphites, or lactones. Single additives or combinations may be used.

The compositions of the present invention may further comprise about 0.01 weight percent to about 5 weight percent of a water scavenger (drying compound). Such water scavengers may comprise ortho esters such as trimethyl-, triethyl-, or tripropylortho formate.

The compositions of the present invention may further comprise an ultra-violet (UV) dye and optionally a solubilizing agent. The UV dye is a useful component for detecting leaks of the refrigerant composition by permitting one to observe the fluorescence of the dye in the refrigerant or heat transfer fluid composition at a leak point in or in the vicinity of refrigeration or air-conditioning apparatus. One may observe the fluorosence of the dye under an ultra-violet light. Solubilizing agents may be needed due to poor solubility of such UV dyes in some refrigerants.

By "ultra-violet" dye is meant a UV fluorescent composition that absorbs light in the ultra-violet or "near" ultra-violet region of the electromagnetic spectrum. The fluorescence produced by the UV fluorescent dye under illumination by a UV light that emits radiation with wavelength anywhere from 10 nanometer to 750 nanometer may be detected. Therefore, if refrigerant containing such a UV fluorescent dye is leaking from a given point in a refrigeration or air conditioning apparatus, the fluorescence can be detected at the leak point. Such UV fluorescent dyes include but are not limited to naphthalimides, perylenes, coumarins, anthracenes, phenanthracenes, xanthenes, thioxanthenes, naphthoxanthenes, fluoresceins, and derivatives or combinations thereof.

Solubilizing agents of the present invention comprise at least one compound selected from the group consisting of hydrocarbons, hydrocarbon ethers, polyoxyalkylene glycol ethers, amides, nitriles, ketones, chlorocarbons, esters, lactones, aryl ethers, fluoroethers and 1,1,1-trifluoroalkanes.

Hydrocarbon solubilizing agents of the present invention comprise hydrocarbons including straight chained, branched chain or cyclic alkanes or alkenes containing 5 or fewer carbon atoms and only hydrogen with no other functional groups. Representative hydrocarbon solubilizing agents comprise propane, propylene, cyclopropane, n-butane, isobutane, and n-pentane. It should be noted that if the refrigerant is a hydrocarbon, then the solubilizing agent may not be the same hydrocarbon.

Hydrocarbon ether solubilizing agents of the present invention comprise ethers containing only carbon, hydrogen and oxygen, such as dimethyl ether (DME).

Polyoxyalkylene glycol ether solubilizing agents of the present invention are represented by the formula $R^1[(OR^2)_xOR^3]_y$, wherein: x is an integer from 1-3; y is an integer from 1-4; $R^1$ is selected from hydrogen and aliphatic hydrocarbon radicals having 1 to 6 carbon atoms and y bonding sites; $R^2$ is selected from aliphatic hydrocarbylene radicals having from 2 to 4 carbon atoms; $R^3$ is selected from hydrogen and aliphatic and alicyclic hydrocarbon radicals having from 1 to 6 carbon atoms; at least one of $R^1$ and $R^3$ is said hydrocarbon radical; and wherein said polyoxyalkylene glycol ethers have a molecular weight of from about 100 to about 300 atomic mass units. In the present polyoxyalkylene glycol ether solubilizing agents represented by $R^1[(OR^2)_xOR^3]_y$: x is preferably 1-2; y is preferably 1; $R^1$ and $R^3$ are preferably independently selected from hydrogen and aliphatic hydrocarbon radicals having 1 to 4 carbon atoms; $R^2$ is preferably selected from aliphatic hydrocarbylene radicals having from 2 or 3 carbon atoms, most preferably 3 carbon atoms; the polyoxyalkylene glycol ether molecular weight is preferably from about 100 to about 250 atomic mass units, most preferably from about 125 to about 250 atomic mass units. The $R^1$ and $R^3$ hydrocarbon radicals having 1 to 6 carbon atoms may be linear, branched or cyclic. Representative $R^1$ and $R^3$ hydrocarbon radicals include methyl, ethyl, propyl, isopropyl, butyl, isobutyl, sec-butyl, tert-butyl, pentyl, isopentyl, neopentyl, tert-pentyl, cyclopentyl, and cyclohexyl. Where free hydroxyl radicals on the present polyoxyalkylene glycol ether solubilizing agents may be incompatible with certain compression refrigeration apparatus materials of construction (e.g. Mylar®), $R^1$ and $R^3$ are preferably aliphatic hydrocarbon radicals having 1 to 4 carbon atoms, most preferably 1 carbon atom. The $R^2$ aliphatic hydrocarbylene radicals having from 2 to 4 carbon atoms form repeating oxyalkylene radicals $—(OR^2)_x—$ that include oxyethylene radicals, oxypropylene radicals, and oxybutylene radicals. The oxyalkylene radical comprising $R^2$ in one polyoxyalkylene glycol ether solubilizing agent molecule may be the same, or one molecule may contain different $R^2$ oxyalkylene groups. The present polyoxyalkylene glycol ether solubilizing agents preferably comprise at least one oxypropylene radical. Where $R^1$ is an aliphatic or alicyclic hydrocarbon radical having 1 to 6 carbon atoms and y bonding sites, the radical may be linear, branched or cyclic. Representative $R^1$ aliphatic hydrocarbon radicals having two bonding sites include, for example, an ethylene radical, a propylene radical, a butylene radical, a pentylene radical, a hexylene radical, a cyclopentylene radical and a cyclohexylene radical. Representative $R^1$ aliphatic hydrocarbon radicals having three or four bonding sites include residues derived from polyalcohols, such as trimethylolpropane, glycerin, pentaerythritol, 1,2,3-trihydroxycyclohexane and 1,3,5-trihydroxycyclohexane, by removing their hydroxyl radicals.

Representative polyoxyalkylene glycol ether solubilizing agents include but are not limited to: $CH_3OCH_2CH(CH_3)O(H$ or $CH_3)$ (propylene glycol methyl (or dimethyl)ether), $CH_3O[CH_2CH(CH_3)O]_2(H$ or $CH_3)$ (dipropylene glycol methyl (or dimethyl)ether), $CH_3O[CH_2CH(CH_3)O]_3(H$ or $CH_3)$ (tripropylene glycol methyl (or dimethyl)ether), $C_2H_5OCH_2CH(CH_3)O(H$ or $C_2H_5)$ (propylene glycol ethyl (or diethyl)ether), $C_2H_5O[CH_2CH(CH_3)O]_2(H$ or $C_2H_5)$ (dipropylene glycol ethyl (or diethyl)ether), $C_2H_5O[CH_2CH(CH_3)O]_3(H$ or $C_2H_5)$ (tripropylene glycol ethyl (or diethyl)ether), $C_3H_7OCH_2CH(CH_3)O(H$ or $C_3H_7)$ (propylene glycol n-propyl (or di-n-propyl)ether), $C_3H_7O[CH_2CH(CH_3)O]_2(H$ or $C_3H_7)$ (dipropylene glycol n-propyl (or di-n-propyl)ether), $C_3H_7O[CH_2CH(CH_3)O]_3(H$ or $C_3H_7)$ (tripropylene glycol n-propyl (or di-n-propyl)ether), $C_4H_9OCH_2CH(CH_3)OH$ (propylene glycol n-butyl ether), $C_4H_9O[CH_2CH(CH_3)O]_2(H$ or $C_4H_9)$ (dipropylene glycol n-butyl (or di-n-butyl)ether), $C_4H_9O[CH_2CH(CH_3)O]_3(H$ or $C_4H_9)$ (tripropylene glycol n-butyl (or di-n-butyl)ether), $(CH_3)_3COCH_2CH(CH_3)OH$ (propylene glycol t-butyl ether), $(CH_3)_3CO[CH_2CH(CH_3)O]_2$ (H or $(CH_3)_3$) (dipropylene glycol t-butyl (or di-t-butyl) ether), $(CH_3)_3CO[CH_2CH(CH_3)O]_3(H$ or $(CH_3)_3)$ (tripropylene glycol t-butyl (or di-t-butyl)ether), $C_5H_{11}OCH_2CH(CH_3)OH$ (propylene glycol n-pentyl ether), $C_4H_9OCH_2CH(C_2H_5)OH$ (butylene glycol n-butyl ether), $C_4H_9O[CH_2CH(C_2H_5)O]_2H$ (dibutylene glycol n-butyl ether), trimethylolpropane tri-n-butyl ether $(C_2H_5C(CH_2O(CH_2)_3CH_3)_3)$ and trimethylolpropane di-n-butyl ether $(C_2H_5C(CH_2OC(CH_2)_3CH_3)_2CH_2OH)$.

Amide solubilizing agents of the present invention comprise those represented by the formulae $R^1CONR^2R^3$ and cyclo-$[R^4CON(R^5)—]$, wherein $R^1$, $R^2$, $R^3$ and $R^5$ are independently selected from aliphatic and alicyclic hydrocarbon radicals having from 1 to 12 carbon atoms; $R^4$ is selected from aliphatic hydrocarbylene radicals having from 3 to 12 carbon atoms; and wherein said amides have a molecular weight of from about 100 to about 300 atomic mass units. The molecular weight of said amides is preferably from about 160 to about 250 atomic mass units. $R^1$, $R^2$, $R^3$ and $R^5$ may optionally include substituted hydrocarbon radicals, that is, radicals containing non-hydrocarbon substituents selected from halogens (e.g., fluorine, chlorine) and alkoxides (e.g. methoxy). $R^1$, $R^2$, $R^3$ and $R^5$ may optionally include heteroatom-substituted hydrocarbon radicals, that is, radicals, which contain the atoms nitrogen (aza-), oxygen (oxa-) or sulfur (thia-) in a radical chain otherwise composed of carbon atoms. In general, no more than three non-hydrocarbon substituents and heteroatoms, and preferably no more than one, will be present for each 10 carbon atoms in $R^{1-3}$, and the presence of any such non-hydrocarbon substituents and heteroatoms must be considered in applying the aforementioned molecular weight limitations. Preferred amide solubilizing agents consist of carbon, hydrogen, nitrogen and oxygen. Representative $R^1$, $R^2$, $R^3$ and $R^5$ aliphatic and alicyclic hydrocarbon radicals include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers. A preferred embodiment of amide solubilizing agents are those wherein $R^4$ in the aforementioned formula cyclo-[$R^4$CON($R^5$)—] may be represented by the hydrocarbylene radical $(CR^6R^7)_n$, in other words, the formula: cyclo-[$(CR^6R^7)_n$CON($R^5$)—] wherein: the previously-stated values for molecular weight apply; n is an integer from 3 to 5; $R^5$ is a saturated hydrocarbon radical containing 1 to 12 carbon atoms; $R^6$ and $R^7$ are independently selected (for each n) by the rules previously offered defining $R^{1-3}$. In the lactams represented by the formula: cyclo-[$(CR^6R^7)_n$CON($R^5$)—], all $R^6$ and $R^7$ are preferably hydrogen, or contain a single saturated hydrocarbon radical among the n methylene units, and $R^5$ is a saturated hydrocarbon radical containing 3 to 12 carbon atoms. For example, 1-(saturated hydrocarbon radical)-5-methylpyrrolidin-2-ones.

Representative amide solubilizing agents include but are not limited to: 1-octylpyrrolidin-2-one, 1-decylpyrrolidin-2-one, 1-octyl-5-methylpyrrolidin-2-one, 1-butylcaprolactam, 1-cyclohexylpyrrolidin-2-one, 1-butyl-5-methylpiperid-2-one, 1-pentyl-5-methylpiperid-2-one, 1-hexylcaprolactam, 1-hexyl-5-methylpyrrolidin-2-one, 5-methyl-1-pentylpiperid-2-one, 1,3-dimethylpiperid-2-one, 1-methylcaprolactam, 1-butyl-pyrrolidin-2-one, 1,5-dimethylpiperid-2-one, 1-decyl-5-methylpyrrolidin-2-one, 1-dodecylpyrrolid-2-one, N,N-dibutylformamide and N,N-diisopropylacetamide.

Ketone solubilizing agents of the present invention comprise ketones represented by the formula $R^1COR^2$, wherein $R^1$ and $R^2$ are independently selected from aliphatic, alicyclic and aryl hydrocarbon radicals having from 1 to 12 carbon atoms, and wherein said ketones have a molecular weight of from about 70 to about 300 atomic mass units. $R^1$ and $R^2$ in said ketones are preferably independently selected from aliphatic and alicyclic hydrocarbon radicals having 1 to 9 carbon atoms. The molecular weight of said ketones is preferably from about 100 to 200 atomic mass units. $R^1$ and $R^2$ may together form a hydrocarbylene radical connected and forming a five, six, or seven-membered ring cyclic ketone, for example, cyclopentanone, cyclohexanone, and cycloheptanone. $R^1$ and $R^2$ may optionally include substituted hydrocarbon radicals, that is, radicals containing non-hydrocarbon substituents selected from halogens (e.g., fluorine, chlorine) and alkoxides (e.g. methoxy). $R^1$ and $R^2$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in $R^1$ and $R^2$, and the presence of any such non-hydrocarbon substituents and heteroatoms must be considered in applying the aforementioned molecular weight limitations. Representative $R^1$ and $R^2$ aliphatic, alicyclic and aryl hydrocarbon radicals in the general formula $R^1COR^2$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl.

Representative ketone solubilizing agents include but are not limited to: 2-butanone, 2-pentanone, acetophenone, butyrophenone, hexanophenone, cyclohexanone, cycloheptanone, 2-heptanone, 3-heptanone, 5-methyl-2-hexanone, 2-octanone, 3-octanone, diisobutyl ketone, 4-ethylcyclohexanone, 2-nonanone, 5-nonanone, 2-decanone, 4-decanone, 2-decalone, 2-tridecanone, dihexyl ketone and dicyclohexyl ketone.

Nitrile solubilizing agents of the present invention comprise nitriles represented by the formula $R^1CN$, wherein $R^1$ is selected from aliphatic, alicyclic or aryl hydrocarbon radicals having from 5 to 12 carbon atoms, and wherein said nitriles have a molecular weight of from about 90 to about 200 atomic mass units. $R^1$ in said nitrile solubilizing agents is preferably selected from aliphatic and alicyclic hydrocarbon radicals having 8 to 10 carbon atoms. The molecular weight of said nitrile solubilizing agents is preferably from about 120 to about 140 atomic mass units. $R^1$ may optionally include substituted hydrocarbon radicals, that is, radicals containing non-hydrocarbon substituents selected from halogens (e.g., fluorine, chlorine) and alkoxides (e.g. methoxy). $R^1$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in $R^1$, and the presence of any such non-hydrocarbon substituents and heteroatoms must be considered in applying the aforementioned molecular weight limitations. Representative $R^1$ aliphatic, alicyclic and aryl hydrocarbon radicals in the general formula $R^1CN$ include pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl. Representative nitrile solubilizing agents include but are not limited to: 1-cyanopentane, 2,2-dimethyl-4-cyanopentane, 1-cyanohexane, 1-cyanoheptane, 1-cyanooctane, 2-cyanooctane, 1-cyanononane, 1-cyanodecane, 2-cyanodecane, 1-cyanoundecane and 1-cyanododecane.

Chlorocarbon solubilizing agents of the present invention comprise chlorocarbons represented by the formula $RCl_x$, wherein; x is selected from the integers 1 or 2; R is selected from aliphatic and alicyclic hydrocarbon radicals having 1 to 12 carbon atoms; and wherein said chlorocarbons have a molecular weight of from about 100 to about 200 atomic mass units. The molecular weight of said chlorocarbon solubilizing agents is preferably from about 120 to 150 atomic mass units. Representative R aliphatic and alicyclic hydrocarbon radicals in the general formula $RCl_x$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers.

Representative chlorocarbon solubilizing agents include but are not limited to: 3-(chloromethyl)pentane, 3-chloro-3-methylpentane, 1-chlorohexane, 1,6-dichlorohexane, 1-chloroheptane, 1-chlorooctane, 1-chlorononane, 1-chlorodecane, and 1,1,1-trichlorodecane.

Ester solubilizing agents of the present invention comprise esters represented by the general formula $R^1CO_2R^2$, wherein $R^1$ and $R^2$ are independently selected from linear and cyclic, saturated and unsaturated, alkyl and aryl radicals. Preferred esters consist essentially of the elements C, H and O, have a molecular weight of from about 80 to about 550 atomic mass units.

Representative esters include but are not limited to: $(CH_3)_2CHCH_2OOC(CH_2)_{2-4}OCOCH_2CH(CH_3)_2$ (diisobutyl dibasic ester), ethyl hexanoate, ethyl heptanoate, n-butyl propionate, n-propyl propionate, ethyl benzoate, di-n-propyl phthalate, benzoic acid ethoxyethyl ester, dipropyl carbonate, "Exxate 700" (a commercial $C_7$ alkyl acetate), "Exxate 800" (a commercial $C_8$ alkyl acetate), dibutyl phthalate, and tert-butyl acetate.

Lactone solubilizing agents of the present invention comprise lactones represented by structures [A], [B], and [C]:

[A]

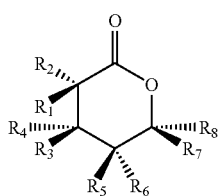

[B]

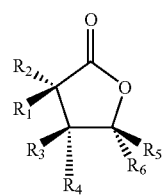

-continued

[C]

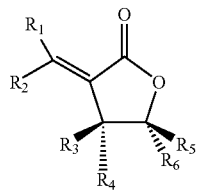

These lactones contain the functional group —$CO_2$— in a ring of six (A), or preferably five atoms (B), wherein for structures [A] and [B], $R_1$ through $R_8$ are independently selected from hydrogen or linear, branched, cyclic, bicyclic, saturated and unsaturated hydrocarbyl radicals. Each $R_1$ though $R_8$ may be connected forming a ring with another $R_1$ through $R_8$. The lactone may have an exocyclic alkylidene group as in structure [C], wherein $R_1$ through $R_6$ are independently selected from hydrogen or linear, branched, cyclic, bicyclic, saturated and unsaturated hydrocarbyl radicals. Each $R_1$ though $R_6$ may be connected forming a ring with another $R_1$ through $R_6$. The lactone solubilizing agents have a molecular weight range of from about 80 to about 300 atomic mass units, preferred from about 80 to about 200 atomic mass units.

Representative lactone solubilizing agents include but are not limited to the compounds listed in Table 4.

TABLE 4

| Additive | Molecular Structure | Molecular Formula | Molecular Weight (amu) |
| --- | --- | --- | --- |
| (E,Z)-3-ethylidene-5-methyl-dihydro-furan-2-one | 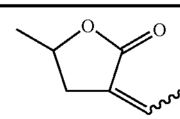 | $C_7H_{10}O_2$ | 126 |
| (E,Z)-3-propylidene-5-methyl-dihydro-furan-2-one | 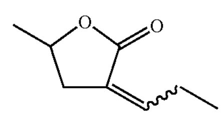 | $C_8H_{12}O_2$ | 140 |
| (E,Z)-3-butylidene-5-methyl-dihydro-furan-2-one | 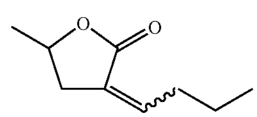 | $C_9H_{14}O_2$ | 154 |
| (E,Z)-3-pentylidene-5-methyl-dihydro-furan-2-one | 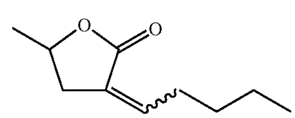 | $C_{10}H_{16}O_2$ | 168 |
| (E,Z)-3-Hexylidene-5-methyl-dihydro-furan-2-one | 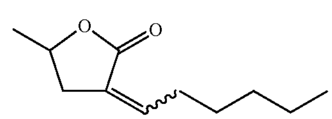 | $C_{11}H_{18}O_2$ | 182 |
| (E,Z)-3-Heptylidene-5-methyl-dihydro-furan-2-one | 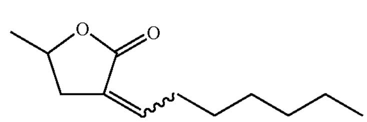 | $C_{12}H_{20}O_2$ | 196 |

TABLE 4-continued

| Additive | Molecular Structure | Molecular Formula | Molecular Weight (amu) |
|---|---|---|---|
| (E,Z)-3-octylidene-5-methyl-dihydro-furan-2-one | 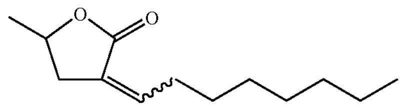 | $C_{13}H_{22}O_2$ | 210 |
| (E,Z)-3-nonylidene-5-methyl-dihydro-furan-2-one | 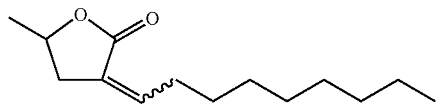 | $C_{14}H_{24}O_2$ | 224 |
| (E,Z)-3-decylidene-5-methyl-dihydro-furan-2-one | 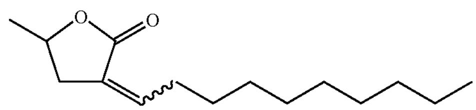 | $C_{15}H_{26}O_2$ | 238 |
| (E,Z)-3-(3,5,5-trimethylhexylidene)-5-methyl-dihydrofuran-2-one | 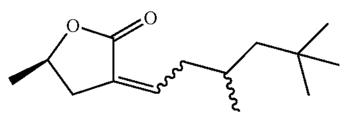 | $C_{14}H_{24}O_2$ | 224 |
| (E,Z)-3-cyclohexylmethylidene-5-methyl-dihydrofuran-2-one | 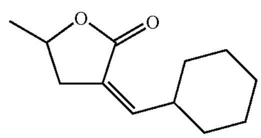 | $C_{12}H_{18}O_2$ | 194 |
| gamma-octalactone | 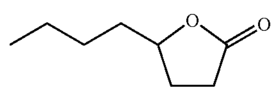 | $C_8H_{14}O_2$ | 142 |
| gamma-nonalactone | 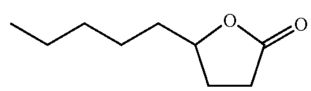 | $C_9H_{16}O_2$ | 156 |
| gamma-decalactone | 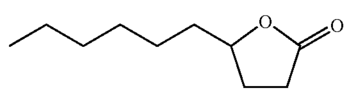 | $C_{10}H_{18}O_2$ | 170 |
| gamma-undecalactone | 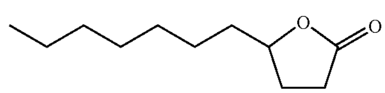 | $C_{11}H_{20}O_2$ | 184 |
| gamma-dodecalactone | 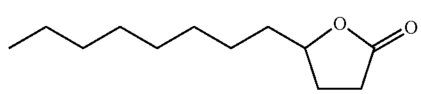 | $C_{12}H_{22}O_2$ | 198 |
| 3-hexyldihydro-furan-2-one | 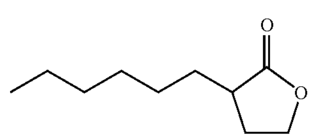 | $C_{10}H_{18}O_2$ | 170 |
| 3-heptyldihydro-furan-2-one | 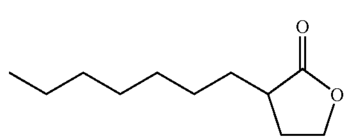 | $C_{11}H_{20}O_2$ | 184 |
| cis-3-ethyl-5-methyl-dihydro-furan-2-one | 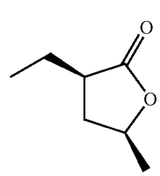 | $C_7H_{12}O_2$ | 128 |

TABLE 4-continued

| Additive | Molecular Formula | Molecular Weight (amu) |
|---|---|---|
| cis-(3-propyl-5-methyl)-dihydro-furan-2-one | $C_8H_{14}O_2$ | 142 |
| cis-(3-butyl-5-methyl)-dihydro-furan-2-one | $C_9H_{16}O_2$ | 156 |
| cis-(3-pentyl-5-methyl)-dihydro-furan-2-one | $C_{10}H_{18}O_2$ | 170 |
| cis-3-hexyl-5-methyl-dihydro-furan-2-one | $C_{11}H_{20}O_2$ | 184 |
| cis-3-heptyl-5-methyl-dihydro-furan-2-one | $C_{12}H_{22}O_2$ | 198 |
| cis-3-octyl-5-methyl-dihydro-furan-2-one | $C_{13}H_{24}O_2$ | 212 |
| cis-3-(3,5,5-trimethylhexyl)-5-methyl-dihydro-furan-2-one | $C_{14}H_{26}O_2$ | 226 |
| cis-3-cyclohexylmethyl-5-methyl-dihydro-furan-2-one | $C_{12}H_{20}O_2$ | 196 |

TABLE 4-continued

| Additive | Molecular Structure | Molecular Formula | Molecular Weight (amu) |
|---|---|---|---|
| 5-methyl-5-hexyl-dihydro-furan-2-one | 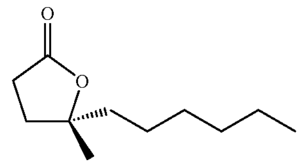 | $C_{11}H_{20}O_2$ | 184 |
| 5-methyl-5-octyl-dihydro-furan-2-one | 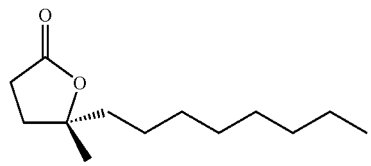 | $C_{13}H_{24}O_2$ | 212 |
| Hexahydro-isobenzofuran-1-one | 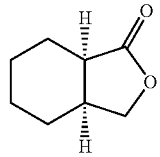 | $C_8H_{12}O_2$ | 140 |
| delta-decalactone | 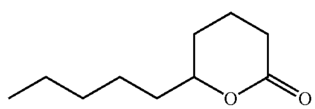 | $C_{10}H_{18}O_2$ | 170 |
| delta-undecalactone | 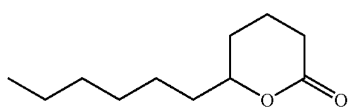 | $C_{11}H_{20}O_2$ | 184 |
| delta-dodecalactone | 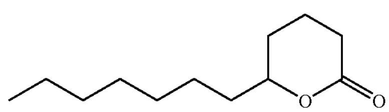 | $C_{12}H_{22}O_2$ | 198 |
| mixture of 4-hexyl-dihydrofuran-2-one and 3-hexyl-dihydro-furan-2-one | | $C_{10}H_{18}O_2$ | 170 |

Lactone solubilizing agents generally have a kinematic viscosity of less than about 7 centistokes at 40° C. For instance, gamma-undecalactone has kinematic viscosity of 5.4 centistokes and cis-(3-hexyl-5-methyl)dihydrofuran-2-one has viscosity of 4.5 centistokes both at 40° C. Lactone solubilizing agents may be available commercially or prepared by methods as described in U.S. patent application Ser. No. 10/910,495 (inventors being P. J. Fagan and C. J. Brandenburg), filed Aug. 3, 2004, incorporated herein by reference.

Aryl ether solubilizing agents of the present invention further comprise aryl ethers represented by the formula $R^1OR^2$, wherein: $R^1$ is selected from aryl hydrocarbon radicals having from 6 to 12 carbon atoms; $R^2$ is selected from aliphatic hydrocarbon radicals having from 1 to 4 carbon atoms; and wherein said aryl ethers have a molecular weight of from about 100 to about 150 atomic mass units. Representative $R^1$ aryl radicals in the general formula $R^1OR^2$ include phenyl, biphenyl, cumenyl, mesityl, tolyl, xylyl, naphthyl and pyridyl. Representative $R^2$ aliphatic hydrocarbon radicals in the general formula $R^1OR^2$ include methyl, ethyl, propyl, isopropyl, butyl, isobutyl, sec-butyl and tert-butyl. Representative aromatic ether solubilizing agents include but are not limited to: methyl phenyl ether (anisole), 1,3-dimethyoxybenzene, ethyl phenyl ether and butyl phenyl ether.

Fluoroether solubilizing agents of the present invention comprise those represented by the general formula $R^1OCF_2CF_2H$, wherein $R^1$ is selected from aliphatic and alicyclic hydrocarbon radicals having from about 5 to about 15 carbon atoms, preferably primary, linear, saturated, alkyl radicals. Representative fluoroether solubilizing agents include but are not limited to: $C_8H_{17}OCF_2CF_2H$ and $C_6H_{13}OCF_2CF_2H$. It should be noted that if the refrigerant is a fluoroether, then the solubilizing agent may not be the same fluoroether.

Fluoroether solubilizing agents may further comprise ethers derived from fluoro-olefins and polyols. The fluoro-olefins may be of the type $CF_2=CXY$, wherein X is hydrogen, chlorine or fluorine, and Y is chlorine, fluorine, $CF_3$ or $OR_f$, wherein $R_f$ is $CF_3$, $C_2F_5$, or $C_3F_7$. Representative fluoro-olefins are tetrafluoroethylene, chlorotrifluoroethylene, hexafluoropropylene, and perfluoromethylvinyl ether. The polyols may be of the type $HOCH_2CRR'(CH_2)_z(CHOH)_x CH_2(CH_2OH)_y$, wherein R and R' are hydrogen or $CH_3$ or $C_2H_5$ and wherein x is an integer from 0-4, y is an integer from 0-3 and z is either zero or 1. Representative polyols are trimethylol propane, pentaerythritol, butane diol, and ethylene glycol.

1,1,1-Trifluoroalkane solubilizing agents of the present invention comprise 1,1,1-trifluoroalkanes represented by the general formula $CF_3R^1$, wherein $R^1$ is selected from aliphatic and alicyclic hydrocarbon radicals having from about 5 to about 15 carbon atoms, preferably primary, linear, saturated, alkyl radicals. Representative 1,1,1-trifluoroalkane solubilizing agents include but are not limited to: 1,1,1-trifluorohexane and 1,1,1-trifluorododecane.

Solubilizing agents of the present invention may be present as a single compound, or may be present as a mixture of more than one solubilizing agent. Mixtures of solubilizing agents may contain two solubilizing agents from the same class of compounds, say two lactones, or two solubilizing agents from two different classes, such as a lactone and a polyoxyalkylene glycol ether.

In the present compositions comprising refrigerant and UV fluorescent dye, from about 0.001 weight percent to about 1.0 weight percent of the composition is UV dye, preferably from about 0.005 weight percent to about 0.5 weight percent, and most preferably from 0.01 weight percent to about 0.25 weight percent.

Solubility of these UV fluorescent dyes in refrigerants may be poor. Therefore, methods for introducing these dyes into the refrigeration or air conditioning apparatus have been awkward, costly and time consuming. U.S. Pat. No. RE 36,951 describes a method, which utilizes a dye powder, solid pellet or slurry of dye that may be inserted into a component of the refrigeration or air conditioning apparatus. As refrigerant and lubricant are circulated through the apparatus, the dye is dissolved or dispersed and carried throughout the apparatus. Numerous other methods for introducing dye into a refrigeration or air conditioning apparatus are described in the literature.

Ideally, the UV fluorescent dye could be dissolved in the refrigerant itself thereby not requiring any specialized method for introduction to the refrigeration or air conditioning apparatus. The present invention relates to compositions including UV fluorescent dye, which may be introduced into the system in the refrigerant. The inventive compositions will allow the storage and transport of dye-containing refrigerant even at low temperatures while maintaining the dye in solution.

In the present compositions comprising refrigerant, UV fluorescent dye and solubilizing agent, from about 1 to about 50 weight percent, preferably from about 2 to about 25 weight percent, and most preferably from about 5 to about 15 weight percent of the combined composition is solubilizing agent in the refrigerant. In the compositions of the present invention the UV fluorescent dye is present in a concentration from about 0.001 weight percent to about 1.0 weight percent in the refrigerant, preferably from 0.005 weight percent to about 0.5 weight percent, and most preferably from 0.01 weight percent to about 0.25 weight percent.

Optionally, commonly used refrigeration system additives may be added, as desired, to compositions of the present invention in order to enhance performance and system stability. These additives are known within the field of refrigeration, and include, but are not limited to, anti wear agents, extreme pressure lubricants, corrosion and oxidation inhibitors, metal surface deactivators, free radical scavengers, and foam control agents. In general, these additives are present in the inventive compositions in small amounts relative to the overall composition. Typically concentrations of from less than about 0.1 weight percent to as much as about 3 weight percent of each additive are used. These additives are selected on the basis of the individual system requirements. These additives include members of the triaryl phosphate family of EP (extreme pressure) lubricity additives, such as butylated triphenyl phosphates (BTPP), or other alkylated triaryl phosphate esters, e.g. Syn-0-Ad 8478 from Akzo Chemicals, tricresyl phosphates and related compounds. Additionally, the metal dialkyl dithiophosphates (e.g. zinc dialkyl dithiophosphate (or ZDDP), Lubrizol 1375 and other members of this family of chemicals may be used in compositions of the present invention. Other antiwear additives include natural product oils and asymmetrical polyhydroxyl lubrication additives, such as Synergol TMS (International Lubricants). Similarly, stabilizers such as anti oxidants, free radical scavengers, and water scavengers may be employed. Compounds in this category can include, but are not limited to, butylated hydroxy toluene (BHT) and epoxides.

Solubilizing agents such as ketones may have an objectionable odor, which can be masked by addition of an odor masking agent or fragrance. Typical examples of odor masking agents or fragrances may include Evergreen, Fresh Lemon, Cherry, Cinnamon, Peppermint, Floral or Orange Peel, available commercially, as well as d-limonene and pinene. Such odor masking agents may be used at concentrations of from about 0.001% to as much as about 15% by weight based on the combined weight of odor masking agent and solubilizing agent.

The present invention further relates to a method of using the refrigerant or heat transfer fluid compositions further comprising ultraviolet fluorescent dye, and optionally, solubilizing agent, in refrigeration or air conditioning apparatus. The method comprises introducing the refrigerant or heat transfer fluid composition into the refrigeration or air conditioning apparatus. This may be done by dissolving the UV fluorescent dye in the refrigerant or heat transfer fluid composition in the presence of a solubilizing agent and introducing the combination into the apparatus. Alternatively, this may be done by combining solubilizing agent and UV fluorescent dye and introducing said combination into refrigeration or air conditioning apparatus containing refrigerant and/or heat transfer fluid. The resulting composition may be used in the refrigeration or air conditioning apparatus.

The present invention further relates to a method of using the refrigerant or heat transfer fluid compositions comprising ultraviolet fluorescent dye to detect leaks. The presence of the dye in the compositions allows for detection of leaking refrigerant in the refrigeration or air conditioning apparatus. Leak detection helps to address, resolve or prevent inefficient operation of the apparatus or system or equipment failure. Leak detection also helps one contain chemicals used in the operation of the apparatus.

The method comprises providing the composition comprising refrigerant, ultra-violet fluorescent dye as described herein, and optionally, a solubilizing agent as described herein, to refrigeration and air conditioning apparatus and employing a suitable means for detecting the UV fluorescent dye-containing refrigerant. Suitable means for detecting the dye include, but are not limited to, ultra-violet lamp, often referred to as a "black light" or "blue light". Such ultra-violet lamps are commercially available from numerous sources specifically designed for this purpose. Once the ultra-violet fluorescent dye containing composition has been introduced to the refrigeration or air conditioning apparatus and has been allowed to circulate throughout the system, a leak can be found by shining said ultra-violet lamp on the apparatus and observing the fluorescence of the dye in the vicinity of any leak point.

The present invention further relates to a method of using the compositions of the present invention for producing refrigeration or heat, wherein the method comprises producing refrigeration by evaporating said composition in the vicinity of a body to be cooled and thereafter condensing said composition; or producing heat by condensing said composition in the vicinity of the body to be heated and thereafter evaporating said composition.

Mechanical refrigeration is primarily an application of thermodynamics wherein a cooling medium, such as a refrigerant, goes through a cycle so that it can be recovered for reuse. Commonly used cycles include vapor-compression, absorption, steam-jet or steam-ejector, and air.

Vapor-compression refrigeration systems include an evaporator, a compressor, a condenser, and an expansion device. A vapor-compression cycle re-uses refrigerant in multiple steps producing a cooling effect in one step and a heating effect in a different step. The cycle can be described simply as follows. Liquid refrigerant enters an evaporator through an expansion device, and the liquid refrigerant boils in the evaporator at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

There are various types of compressors that may be used in refrigeration applications. Compressors can be generally classified as reciprocating, rotary, jet, centrifugal, scroll, screw or axial-flow, depending on the mechanical means to compress the fluid, or as positive-displacement (e.g., reciprocating, scroll or screw) or dynamic (e.g., centrifugal or jet), depending on how the mechanical elements act on the fluid to be compressed.

Either positive displacement or dynamic compressors may be used in the present inventive process. A centrifugal type compressor is the preferred equipment for the present refrigerant compositions.

A centrifugal compressor uses rotating elements to accelerate the refrigerant radially, and typically includes an impeller and diffuser housed in a casing. Centrifugal compressors usually take fluid in at an impeller eye, or central inlet of a circulating impeller, and accelerate it radially outward. Some static pressure rise occurs in the impeller, but most of the pressure rise occurs in the diffuser section of the casing, where velocity is converted to static pressure. Each impeller-diffuser set is a stage of the compressor. Centrifugal compressors are built with from 1 to 12 or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities.

Positive displacement compressors draw vapor into a chamber, and the chamber decreases in volume to compress the vapor. After being compressed, the vapor is forced from the chamber by further decreasing the volume of the chamber to zero or nearly zero. A positive displacement compressor can build up a pressure, which is limited only by the volumetric efficiency and the strength of the parts to withstand the pressure.

Unlike a positive displacement compressor, a centrifugal compressor depends entirely on the centrifugal force of the high-speed impeller to compress the vapor passing through the impeller. There is no positive displacement, but rather what is called dynamic-compression.

The pressure a centrifugal compressor can develop depends on the tip speed of the impeller. Tip speed is the speed of the impeller measured at its tip and is related to the diameter of the impeller and its revolutions per minute. The capacity of the centrifugal compressor is determined by the size of the passages through the impeller. This makes the size of the compressor more dependent on the pressure required than the capacity.

Because of its high-speed operation, a centrifugal compressor is fundamentally a high volume, low-pressure machine. A centrifugal compressor works best with a low-pressure refrigerant, such as trichlorofluoromethane (CFC-11) or 1,2,2-trichlorotrifluoroethane (CFC-113).

Large centrifugal compressors typically operate at 3000 to 7000 revolutions per minute (rpm). Small turbine centrifugal compressors are designed for high speeds, from about 40,000 to about 70,000 (rpm), and have small impeller sizes, typically less than 0.15 meters.

A multi-stage impeller may be used in a centrifugal compressor to improve compressor efficiency thus requiring less power in use. For a two-stage system, in operation, the discharge of the first stage impeller goes to the suction intake of a second impeller. Both impellers may operate by use of a single shaft (or axle). Each stage can build up a compression ratio of about 4 to 1; that is, the absolute discharge pressure can be four times the absolute suction pressure. An example of a two-stage centrifugal compressor system, in this case for automotive applications, is described in U.S. Pat. No. 5,065,990, incorporated herein by reference.

The compositions of the present invention suitable for use in a refrigeration or air conditioning systems employing a centrifugal compressor are selected from the group consisting of at least one of:

1,1,1,2,2,4,5,5,5-nonafluoro-4-(trifluoromethyl)-3-pentanone and 1,1,3-trifluoropropane;
1,1,1,2,2,4,5,5,5-nonafluoro-4-(trifluoromethyl)-3-pentanone and 1,3-difluoropropane;
1,1,1,2,2,4,5,5,5-nonafluoro-4-(trifluoromethyl)-3-pentanone and 1,1,1,3,3-pentafluorobutane;
1,1,1,2,2,4,5,5,5-nonafluoro-4-(trifluoromethyl)-3-pentanone and 1,1-difluorobutane;
1,1,1,2,2,4,5,5,5-nonafluoro-4-(trifluoromethyl)-3-pentanone and 1,2-difluorobutane;
1,1,1,2,2,4,5,5,5-nonafluoro-4-(trifluoromethyl)-3-pentanone and 1,3-difluorobutane;
1,1,1,2,2,4,5,5,5-nonafluoro-4-(trifluoromethyl)-3-pentanone and 1,4-difluorobutane;

1,1,1,2,2,4,5,5,5-nonafluoro-4-(trifluoromethyl)-3-pentanone and 1,3-difluoro-2-methylpropane;
1,1,1,2,2,4,5,5,5-nonafluoro-4-(trifluoromethyl)-3-pentanone and 1,2-difluoro-2-methylpropane;
1,1,1,2,2,4,5,5,5-nonafluoro-4-(trifluoromethyl)-3-pentanone and 2,3-difluorobutane;
1,1,1,2,2,4,5,5,5-nonafluoro-4-(trifluoromethyl)-3-pentanone and 1,1,1-trifluoropentane;
1,1,1,2,2,4,5,5,5-nonafluoro-4-(trifluoromethyl)-3-pentanone and 1,1,1-trifluoro-3-methylbutane;
1,1,1,2,2,4,5,5,5-nonafluoro-4-(trifluoromethyl)-3-pentanone and 1,1-difluoropentane;
1,1,1,2,2,4,5,5,5-nonafluoro-4-(trifluoromethyl)-3-pentanone and 1,2-difluoropentane;
1,1,1,2,2,4,5,5,5-nonafluoro-4-(trifluoromethyl)-3-pentanone and 2,2-difluoropentane;
1,1,1,2,2,4,5,5,5-nonafluoro-4-(trifluoromethyl)-3-pentanone and 1,1,1,2,2,3,4,5,5,5-decafluoropentane;
1,1,1,2,2,4,5,5,5-nonafluoro-4-(trifluoromethyl)-3-pentanone and 1,1,1-trifluorohexane;
1,1,1,2,2,4,5,5,5-nonafluoro-4-(trifluoromethyl)-3-pentanone and 1,1,2,2-tetrafluorocyclobutane; and
1,1,1,2,2,4,5,5,5-nonafluoro-4-(trifluoromethyl)-3-pentanone and 3,3,4,4,5,5,6,6-nonafluoro-1-hexene.

These above-listed compositions are also suitable for use in a multi-stage centrifugal compressor, preferably a two-stage centrifugal compressor apparatus.

The compositions of the present invention may be used in stationary air-conditioning, heat pumps or mobile air-conditioning and refrigeration systems. Stationary air conditioning and heat pump applications include window, ductless, ducted, packaged terminal, chillers and commercial, including packaged rooftop. Refrigeration applications include domestic or home refrigerators and freezers, ice machines, self-contained coolers and freezers, walk-in coolers and freezers and transport refrigeration systems.

The compositions of the present invention may additionally be used in air-conditioning, heating and refrigeration systems that employ fin and tube heat exchangers, microchannel heat exchangers and vertical or horizontal single pass tube or plate type heat exchangers.

Conventional microchannel heat exchangers may not be ideal for the low pressure refrigerant compositions of the present invention. The low operating pressure and density result in high flow velocities and high frictional losses in all components. In these cases, the evaporator design may be modified. Rather than several microchannel slabs connected in series (with respect to the refrigerant path) a single slab/single pass heat exchanger arrangement may be used. Therefore, a preferred heat exchanger for the low pressure refrigerants of the present invention is a single slab/single pass heat exchanger.

In addition to two-stage compressor systems, the following compositions of the present invention are suitable for use in refrigeration or air conditioning systems employing a single slab/single pass heat exchanger:
1,1,1,2,2,4,5,5,5-nonafluoro-4-(trifluoromethyl)-3-pentanone and 1,1,3-trifluoropropane;
1,1,1,2,2,4,5,5,5-nonafluoro-4-(trifluoromethyl)-3-pentanone and 1,3-difluoropropane;
1,1,1,2,2,4,5,5,5-nonafluoro-4-(trifluoromethyl)-3-pentanone and 1,1,1,3,3-pentafluorobutane;
1,1,1,2,2,4,5,5,5-nonafluoro-4-(trifluoromethyl)-3-pentanone and 1,1-difluorobutane;
1,1,1,2,2,4,5,5,5-nonafluoro-4-(trifluoromethyl)-3-pentanone and 1,2-difluorobutane;
1,1,1,2,2,4,5,5,5-nonafluoro-4-(trifluoromethyl)-3-pentanone and 1,3-difluorobutane;
1,1,1,2,2,4,5,5,5-nonafluoro-4-(trifluoromethyl)-3-pentanone and 1,4-difluorobutane;
1,1,1,2,2,4,5,5,5-nonafluoro-4-(trifluoromethyl)-3-pentanone and 1,3-difluoro-2-methylpropane;
1,1,1,2,2,4,5,5,5-nonafluoro-4-(trifluoromethyl)-3-pentanone and 1,2-difluoro-2-methylpropane;
1,1,1,2,2,4,5,5,5-nonafluoro-4-(trifluoromethyl)-3-pentanone and 2,3-difluorobutane;
1,1,1,2,2,4,5,5,5-nonafluoro-4-(trifluoromethyl)-3-pentanone and 1,1,1-trifluoropentane;
1,1,1,2,2,4,5,5,5-nonafluoro-4-(trifluoromethyl)-3-pentanone and 1,1,1-trifluoro-3-methylbutane;
1,1,1,2,2,4,5,5,5-nonafluoro-4-(trifluoromethyl)-3-pentanone and 1,1-difluoropentane;
1,1,1,2,2,4,5,5,5-nonafluoro-4-(trifluoromethyl)-3-pentanone and 1,2-difluoropentane;
1,1,1,2,2,4,5,5,5-nonafluoro-4-(trifluoromethyl)-3-pentanone and 2,2-difluoropentane;
1,1,1,2,2,4,5,5,5-nonafluoro-4-(trifluoromethyl)-3-pentanone and 1,1,1,2,2,3,4,5,5,5-decafluoropentane;
1,1,1,2,2,4,5,5,5-nonafluoro-4-(trifluoromethyl)-3-pentanone and 1,1,1-trifluorohexane;
1,1,1,2,2,4,5,5,5-nonafluoro-4-(trifluoromethyl)-3-pentanone and 1,1,2,2-tetrafluorocyclobutane;
1,1,1,2,2,4,5,5,5-nonafluoro-4-(trifluoromethyl)-3-pentanone and 3,3,4,4,5,5,6,6-nonafluoro-1-hexene.

The compositions of the present invention are particularly useful in small turbine centrifugal compressors, which can be used in auto and window air conditioning or heat pump as well as other applications. These high efficiency miniature centrifugal compressors may be driven by an electric motor and can therefore be operated independently of the engine speed. A constant compressor speed allows the system to provide a relatively constant cooling capacity at all engine speeds. This provides an opportunity for efficiency improvements especially at higher engine speeds as compared to a conventional R-134a automobile air-conditioning system. When the cycling operation of conventional systems at high driving speeds is taken into account, the advantage of these low pressure systems becomes even greater.

Some of the low pressure refrigerant fluids of the present invention may be suitable as drop-in replacements for CFC-113 in existing centrifugal equipment.

The present invention relates to a process for producing refrigeration comprising evaporating the compositions of the present invention in the vicinity of a body to be cooled, and thereafter condensing said compositions.

The present invention further relates to a process for producing heat comprising condensing the compositions of the present invention in the vicinity of a body to be heated, and thereafter evaporating said compositions.

The present invention further relates to a process for transfer of heat from a heat source to a heat sink wherein the compositions of the present invention serve as heat transfer fluids. Said process for heat transfer comprises transferring the compositions of the present invention from a heat source to a heat sink.

Heat transfer fluids are utilized to transfer, move or remove heat from one space, location, object or body to a different space, location, object or body by radiation, conduction, or convection. A heat transfer fluid may function as a secondary coolant by providing means of transfer for cooling (or heating) from a remote refrigeration (or heating) system. In some systems, the heat transfer fluid may remain in a constant state throughout the transfer process (i.e., not evaporate or condense). Alternatively, evaporative cooling processes may utilize heat transfer fluids as well.

A heat source may be defined as any space, location, object or body from which it is desirable to transfer, move or remove heat. Examples of heat sources may be spaces (open or enclosed) requiring refrigeration or cooling, such as refrigerator or freezer cases in a supermarket, building spaces requiring air conditioning, or the passenger compartment of an automobile requiring air conditioning. A heat sink may be defined as any space, location, object or body capable of absorbing heat. A vapor compression refrigeration system is one example of such a heat sink.

EXAMPLES

Example 1

Impact of Vapor Leakage

A vessel is charged with an initial composition at a specified temperature, and the initial vapor pressure of the composition is measured. The composition is allowed to leak from the vessel, while the temperature is held constant, until 50 weight percent of the initial composition is removed, at which time the vapor pressure of the composition remaining in the vessel is measured. The results are summarized in Table 5 below.

TABLE 5

| Compounds wt % A/wt % B | Initial Psia | Initial kPa | After 50% Leak Psia | After 50% Leak kPa | Delta P % |
|---|---|---|---|---|---|
| PEIK/HFC-263fa (46.0° C.) | | | | | |
| 78.4/21.6 | 14.67 | 101.15 | 14.67 | 101.15 | 0.0% |
| 85/15 | 14.68 | 101.22 | 14.68 | 101.22 | 0.0% |
| 90/10 | 14.69 | 101.28 | 14.69 | 101.28 | 0.0% |
| 95/5 | 14.59 | 100.60 | 14.56 | 100.39 | 0.2% |
| 99/1 | 14.13 | 97.42 | 13.52 | 93.22 | 4.3% |
| 100/0 | 13.24 | 91.29 | 13.24 | 91.29 | 0.0% |
| 70/30 | 14.69 | 101.28 | 14.69 | 101.28 | 0.0% |
| 60/40 | 14.75 | 101.70 | 14.74 | 101.63 | 0.1% |
| 40/60 | 14.91 | 102.80 | 14.90 | 102.73 | 0.1% |
| 20/80 | 15.06 | 103.84 | 15.05 | 103.77 | 0.1% |
| 10/90 | 15.13 | 104.32 | 15.12 | 104.25 | 0.1% |
| 1/99 | 15.18 | 104.66 | 15.18 | 104.66 | 0.0% |
| 0/100 | 15.19 | 104.73 | 15.19 | 104.73 | 0.0% |
| PEIK/HFC-272fa (33.5° C.) | | | | | |
| 74.7/25.3 | 14.68 | 101.22 | 14.68 | 101.22 | 0.0% |
| 90/10 | 14.28 | 98.46 | 13.13 | 90.53 | 8.1% |
| 91/9 | 14.20 | 97.91 | 12.58 | 86.74 | 11.4% |
| 100/0 | 8.32 | 57.36 | 8.32 | 57.36 | 0.0% |
| 60/40 | 14.48 | 99.84 | 14.16 | 97.63 | 2.2% |
| 40/60 | 13.74 | 94.73 | 12.75 | 87.91 | 7.2% |
| 20/80 | 12.66 | 87.29 | 11.80 | 81.36 | 6.8% |
| 10/90 | 12.04 | 83.01 | 11.55 | 79.63 | 4.1% |
| 1/99 | 11.45 | 78.95 | 11.40 | 78.60 | 0.4% |
| 0/100 | 11.39 | 78.53 | 11.39 | 78.53 | 0.0% |
| PEIK/HFC-365mfc (50.0° C.) | | | | | |
| 0/100 | 20.23 | 139.48 | 20.23 | 139.48 | 0.0% |
| 1/99 | 20.23 | 139.48 | 20.23 | 139.48 | 0.0% |
| 20/80 | 20.14 | 138.86 | 20.13 | 138.79 | 0.0% |
| 40/60 | 19.82 | 136.65 | 19.75 | 136.17 | 0.4% |
| 60/40 | 19.16 | 132.10 | 18.94 | 130.59 | 1.1% |
| 80/20 | 17.87 | 123.21 | 17.48 | 120.52 | 2.2% |
| 99/1 | 15.41 | 106.25 | 15.36 | 105.90 | 0.3% |
| 100/0 | 15.23 | 105.01 | 15.23 | 105.01 | 0.0% |
| PEIK/HFC-392p (37.6° C.) | | | | | |
| 50.6/49.4 | 14.71 | 101.42 | 14.71 | 101.42 | 0.0% |
| 80/20 | 13.92 | 95.98 | 13.36 | 92.11 | 4.0% |

TABLE 5-continued

| Compounds wt % A/wt % B | Initial Psia | Initial kPa | After 50% Leak Psia | After 50% Leak kPa | Delta P % |
|---|---|---|---|---|---|
| 90/10 | 12.70 | 87.56 | 11.75 | 81.01 | 7.5% |
| 99/1 | 10.18 | 70.19 | 9.92 | 68.40 | 2.6% |
| 100/0 | 9.74 | 67.16 | 9.74 | 67.16 | 0.0% |
| 20/80 | 14.31 | 98.66 | 14.11 | 97.29 | 1.4% |
| 10/90 | 13.99 | 96.46 | 13.81 | 95.22 | 1.3% |
| 1/99 | 13.61 | 93.84 | 13.58 | 93.63 | 0.2% |
| 0/100 | 13.56 | 93.49 | 13.56 | 93.49 | 0.0% |
| PEIK/HFC-392qe (37.2° C.) | | | | | |
| 78.4/21.6 | 14.67 | 101.15 | 14.67 | 101.15 | 0.0% |
| 90/10 | 14.42 | 99.42 | 13.59 | 93.70 | 5.8% |
| 91/9 | 14.34 | 98.87 | 13.18 | 90.87 | 8.1% |
| 92/8 | 14.25 | 98.25 | 12.65 | 87.22 | 11.2% |
| 100/0 | 9.59 | 66.12 | 9.59 | 66.12 | 0.0% |
| 60/40 | 14.38 | 99.15 | 13.60 | 93.77 | 5.4% |
| 54/46 | 14.17 | 97.70 | 12.81 | 88.32 | 9.6% |
| 53/37 | 14.12 | 97.35 | 12.67 | 87.36 | 10.3% |
| 0/100 | 9.56 | 65.91 | 9.56 | 65.91 | 0.0% |
| PEIK/HFC-392qfe (41.3° C.) | | | | | |
| 84.9/15.1 | 14.71 | 101.42 | 14.71 | 101.42 | 0.0% |
| 95/5 | 14.21 | 97.98 | 12.92 | 89.08 | 9.1% |
| 96/4 | 13.99 | 96.46 | 12.37 | 85.29 | 11.6% |
| 100/0 | 11.18 | 77.08 | 11.18 | 77.08 | 0.0% |
| 65/35 | 14.27 | 98.39 | 12.95 | 89.29 | 9.3% |
| 64/36 | 14.23 | 98.11 | 12.76 | 87.98 | 10.3% |
| 0/100 | 7.91 | 54.54 | 7.91 | 54.54 | 0.0% |
| PEIK/HFC-392qff (45.8° C.) | | | | | |
| 92.5/7.5 | 14.71 | 101.42 | 14.71 | 101.42 | 0.0% |
| 99/1 | 13.89 | 95.77 | 13.40 | 92.39 | 3.5% |
| 100/0 | 13.15 | 90.67 | 13.15 | 90.67 | 0.0% |
| 80/20 | 14.40 | 99.29 | 13.69 | 94.39 | 4.9% |
| 76/24 | 14.24 | 98.18 | 12.87 | 88.74 | 9.6% |
| 75/25 | 14.20 | 97.91 | 12.62 | 87.01 | 11.1% |
| 0/100 | 5.03 | 34.68 | 5.03 | 34.68 | 0.0% |
| PEIK/HFC-392qqz (41.7° C.) | | | | | |
| 86.8/13.2 | 14.68 | 101.22 | 14.68 | 101.22 | 0.0% |
| 95/5 | 14.35 | 98.94 | 13.26 | 91.43 | 7.6% |
| 96/4 | 14.18 | 97.77 | 12.64 | 87.15 | 10.9% |
| 100/0 | 11.34 | 78.19 | 11.34 | 78.19 | 0.0% |
| 70/30 | 14.34 | 98.87 | 13.27 | 91.49 | 7.5% |
| 68/32 | 14.26 | 98.32 | 12.88 | 88.81 | 9.7% |
| 67/33 | 14.22 | 98.04 | 12.67 | 87.36 | 10.9% |
| 0/100 | 7.26 | 50.06 | 7.26 | 50.06 | 0.0% |
| PEIK/HFC-392qy (31.5° C.) | | | | | |
| 55.9/44.1 | 14.69 | 101.28 | 14.69 | 101.28 | 0.0% |
| 80/20 | 14.16 | 97.63 | 13.36 | 92.11 | 5.6% |
| 84/16 | 13.86 | 95.56 | 12.47 | 85.98 | 10.0% |
| 100/0 | 7.70 | 53.09 | 7.70 | 53.09 | 0.0% |
| 40/60 | 14.56 | 100.39 | 14.41 | 99.35 | 1.0% |
| 20/80 | 14.02 | 96.67 | 13.66 | 94.18 | 2.6% |
| 10/90 | 13.60 | 93.77 | 13.33 | 91.91 | 2.0% |
| 1/99 | 13.14 | 90.60 | 13.10 | 90.32 | 0.3% |
| 0/100 | 13.08 | 90.18 | 13.08 | 90.18 | 0.0% |
| PEIK/HFC-392see (36.0° C.) | | | | | |
| 75.0/25.0 | 14.71 | 101.42 | 14.71 | 101.42 | 0.0% |
| 90/10 | 14.29 | 98.53 | 12.94 | 89.22 | 9.4% |
| 91/9 | 14.18 | 97.77 | 12.44 | 85.77 | 12.3% |
| 100/0 | 9.16 | 63.16 | 9.16 | 63.16 | 0.0% |
| 48/52 | 14.16 | 97.63 | 12.79 | 88.18 | 9.7% |
| 47/53 | 14.12 | 97.35 | 12.66 | 87.29 | 10.3% |
| 0/100 | 10.19 | 70.26 | 10.19 | 70.26 | 0.0% |
| PEIK/HFC-4-10-3m (36.2° C.) | | | | | |
| 47.5/52.5 | 14.70 | 101.35 | 14.70 | 101.35 | 0.0% |
| 60/40 | 14.60 | 100.66 | 14.51 | 100.04 | 0.6% |
| 80/20 | 13.71 | 94.53 | 12.83 | 88.46 | 6.4% |
| 86/14 | 13.04 | 89.91 | 11.78 | 81.22 | 9.7% |
| 87/13 | 12.89 | 88.87 | 11.58 | 79.84 | 10.2% |
| 100/0 | 9.24 | 63.71 | 9.24 | 63.71 | 0.0% |
| 20/80 | 14.29 | 98.53 | 14.07 | 97.01 | 1.5% |

TABLE 5-continued

| Compounds wt % A/wt % B | Initial Psia | Initial kPa | After 50% Leak Psia | After 50% Leak kPa | Delta P % |
|---|---|---|---|---|---|
| 10/90 | 13.91 | 95.91 | 13.69 | 94.39 | 1.6% |
| 1/99 | 13.43 | 92.60 | 13.39 | 92.32 | 0.3% |
| 0/100 | 13.37 | 92.18 | 13.37 | 92.18 | 0.0% |
| PEIK/HFC-4-10-3mfsz (35.4° C.) | | | | | |
| 45.4/54.6 | 14.67 | 101.15 | 14.67 | 101.15 | 0.0% |
| 80/20 | 13.58 | 93.63 | 12.59 | 86.81 | 7.3% |
| 84/16 | 13.15 | 90.67 | 11.89 | 81.98 | 9.6% |
| 85/15 | 13.02 | 89.77 | 11.69 | 80.60 | 10.2% |
| 100/0 | 8.96 | 61.78 | 8.96 | 61.78 | 0.0% |
| 20/80 | 14.33 | 98.80 | 14.14 | 97.49 | 1.3% |
| 10/90 | 13.98 | 96.39 | 13.78 | 95.01 | 1.4% |
| 1/99 | 13.53 | 93.29 | 13.50 | 93.08 | 0.2% |
| 0/100 | 13.47 | 92.87 | 13.47 | 92.87 | 0.0% |
| PEIK/HFC-4-11-2p (48.7° C.) | | | | | |
| 95.2/4.8 | 14.70 | 101.35 | 14.70 | 101.35 | 0.0% |
| 99/1 | 14.62 | 100.80 | 14.62 | 100.80 | 0.0% |
| 100/0 | 14.56 | 100.39 | 14.56 | 100.39 | 0.0% |
| 80/20 | 14.16 | 97.63 | 13.86 | 95.56 | 2.1% |
| 62/38 | 13.18 | 90.87 | 11.94 | 82.32 | 9.4% |
| 61/39 | 13.13 | 90.53 | 11.81 | 81.43 | 10.1% |
| 0/100 | 7.55 | 52.06 | 7.55 | 52.06 | 0.0% |
| PEIK/HFC-4-11-2qe (44.8° C.) | | | | | |
| 90.1/9.9 | 14.68 | 101.22 | 14.68 | 101.22 | 0.0% |
| 99/1 | 13.51 | 93.15 | 12.88 | 88.81 | 4.7% |
| 100/0 | 12.69 | 87.50 | 12.69 | 87.50 | 0.0% |
| 72/28 | 14.29 | 98.53 | 13.02 | 89.77 | 8.9% |
| 71/29 | 14.26 | 98.32 | 12.79 | 88.18 | 10.3% |
| 0/100 | 5.39 | 37.16 | 5.39 | 37.16 | 0.0% |
| PEIK/HFC-4-11-2sc (45.2° C.) | | | | | |
| 82.0/18.0 | 14.69 | 101.28 | 14.69 | 101.28 | 0.0% |
| 90/10 | 14.50 | 99.97 | 14.37 | 99.08 | 0.9% |
| 99/1 | 13.19 | 90.94 | 13.05 | 89.98 | 1.1% |
| 100/0 | 12.87 | 88.74 | 12.87 | 88.74 | 0.0% |
| 60/40 | 14.20 | 97.91 | 13.58 | 93.63 | 4.4% |
| 51/49 | 13.86 | 95.56 | 12.55 | 86.53 | 9.5% |
| 50/50 | 13.81 | 95.22 | 12.41 | 85.56 | 10.1% |
| 0/100 | 9.12 | 62.88 | 9.12 | 62.88 | 0.0% |
| PEIK/HFC-43-10mee (46.0° C.) | | | | | |
| 73.6/26.4 | 14.69 | 101.28 | 14.69 | 101.28 | 0.0% |
| 90/10 | 14.31 | 98.66 | 14.12 | 97.35 | 1.3% |
| 99/1 | 13.41 | 92.46 | 13.33 | 91.91 | 0.6% |
| 100/0 | 13.24 | 91.29 | 13.24 | 91.29 | 0.0% |
| 40/60 | 13.81 | 95.22 | 13.28 | 91.56 | 3.8% |
| 20/80 | 12.52 | 86.32 | 11.79 | 81.29 | 5.8% |
| 10/90 | 11.65 | 80.32 | 11.14 | 76.81 | 4.4% |
| 1/99 | 10.73 | 73.98 | 10.67 | 73.57 | 0.6% |
| 0/100 | 10.62 | 73.22 | 10.62 | 73.22 | 0.0% |
| PEIK/HFC-5-12-3m (48.8° C.) | | | | | |
| 96.0/4.0 | 14.71 | 101.42 | 14.71 | 101.42 | 0.0% |
| 99/1 | 14.66 | 101.08 | 14.65 | 101.01 | 0.1% |
| 100/0 | 14.61 | 100.73 | 14.61 | 100.73 | 0.0% |
| 80/20 | 14.12 | 97.35 | 13.76 | 94.87 | 2.5% |
| 65/35 | 13.29 | 91.63 | 12.01 | 82.81 | 9.6% |
| 64/36 | 13.24 | 91.29 | 11.86 | 81.77 | 10.4% |
| 0/100 | 6.17 | 42.54 | 6.17 | 42.54 | 0.0% |
| PEIK/HFC-C354cc (48.7° C.) | | | | | |
| 73.2/26.8 | 14.72 | 101.49 | 14.72 | 101.49 | 0.0% |
| 90/10 | 14.66 | 101.08 | 14.66 | 101.08 | 0.0% |
| 99/1 | 14.57 | 100.46 | 14.57 | 100.46 | 0.0% |
| 100/0 | 14.56 | 100.39 | 14.56 | 100.39 | 0.0% |
| 40/60 | 14.56 | 100.39 | 14.55 | 100.32 | 0.1% |
| 20/80 | 14.37 | 99.08 | 14.35 | 98.94 | 0.1% |
| 1/99 | 14.13 | 97.42 | 14.13 | 97.42 | 0.0% |
| 0/100 | 14.11 | 97.29 | 14.11 | 97.29 | 0.0% |
| PEIK/PFBE (50° C.) | | | | | |
| 0/100 | 10.79 | 74.39 | 10.79 | 74.39 | 0.0% |
| 1/99 | 10.86 | 74.88 | 10.84 | 74.74 | 0.2% |
| 10/90 | 11.38 | 78.46 | 11.19 | 77.15 | 1.7% |
| 20/80 | 11.93 | 82.25 | 11.62 | 80.12 | 2.6% |
| 30/70 | 12.43 | 85.70 | 12.09 | 83.36 | 2.7% |
| 40/60 | 12.91 | 89.01 | 12.57 | 86.67 | 2.6% |
| 50/50 | 13.35 | 92.05 | 13.06 | 90.05 | 2.2% |
| 60/40 | 13.78 | 95.01 | 13.54 | 93.36 | 1.7% |
| 70/30 | 14.17 | 97.70 | 14.01 | 96.60 | 1.1% |
| 80/20 | 14.55 | 100.32 | 14.45 | 99.63 | 0.7% |
| 90/10 | 14.90 | 102.73 | 14.86 | 102.46 | 0.3% |
| 99/1 | 15.20 | 104.80 | 15.20 | 104.80 | 0.0% |
| 100/0 | 15.23 | 105.01 | 15.23 | 105.01 | 0.0% |

The results show the difference in vapor pressure between the original composition and the composition remaining after 50 weight percent has been removed is less then about 10 percent for compositions of the present invention. This indicates compositions of the present invention are azeotropic or near-azeotropic. Where an azeotrope is present, the data show compositions of the present invention have an initial vapor pressure higher than the vapor pressure of either pure component.

Example 2

Tip Speed to Develop Pressure

Tip speed can be estimated by making some fundamental relationships for refrigeration equipment that use centrifugal compressors. The torque an impeller ideally imparts to a gas is defined as $$T = m*(v_2*r_2 - v_1*r_1) \quad \text{Equation 1}$$

where
T=torque, N*m
m=mass rate of flow, kg/s
$v_2$=tangential velocity of refrigerant leaving impeller (tip speed), m/s
$r_2$=radius of exit impeller, m
$v_1$=tangential velocity of refrigerant entering impeller, m/s
$r_1$=radius of inlet of impeller, m Assuming the refrigerant enters the impeller in an essentially radial direction, the tangential component of the velocity v1=0, therefore $$T = m*v2*r2 \quad \text{Equation 2}$$

The power required at the shaft is the product of the torque and the rotative speed $$P = T*w \quad \text{Equation 3}$$

where
P=power, W
w=rotative speed, rez/s therefore, $$P = T*w = m*v_2*r_2*w \quad \text{Equation 4}$$

At low refrigerant flow rates, the tip speed of the impeller and the tangential velocity of the refrigerant are nearly identical; therefore $$r_2*w = v_2 \quad \text{Equation 5}$$

and $$P = m*v2*v_2 \quad \text{Equation 6}$$

Another expression for ideal power is the product of the mass rate of flow and the isentropic work of compression, $$P = m * H_i * (1000 \text{ J/kJ})$$ Equation 7 where $H_i$=Difference in enthalpy of the refrigerant from a saturated vapor at the evaporating conditions to saturated condensing conditions, kJ/kg.

Combining the two expressions Equation 6 and 7 produces, $$v_2 * v_2 = 1000 * H_i$$ Equation 8

Although Equation 8 is based on some fundamental assumptions, it provides a good estimate of the tip speed of the impeller and provides an important way to compare tip speeds of refrigerants.

Table 6 below shows theoretical tip speeds that are calculated for 1,2,2-trichlorotrifluoroethane (CFC-113) and compositions of the present invention. The conditions assumed for this comparison are:

Evaporator temperature 40.0° F. (4.4° C.)
Condenser temperature 110.0° F. (43.3° C.)
Liquid subcool temperature 10.0° F. (5.5° C.)
Return gas temperature 75.0° F. (23.8° C.)
Compressor efficiency is 70%

These are typical conditions under which small turbine centrifugal compressors perform.

The example shows that compounds of the present invention have tip speeds within about +/−20 percent of CFC-113 and would be effective replacements for CFC-113 with minimal compressor design changes. Most preferred compositions have tip speeds within about +/−10 percent of CFC-113.

Example 3

Performance Data

The data in table 7 shows the performance of various refrigerants compared to CFC-113. The data are based on the following conditions.

| Evaporator temperature | 40.0° F. (4.4° C.) |
| Condenser temperature | 110.0° F. (43.3° C.) |
| Subcool temperature | 10.0° F. (5.5° C.) |
| Compressor efficiency is | 70% |

TABLE 6

| Refrigerant composition | Wt % PEIK | Wt % B | Hi Btu/lb | Hi * 0.7 Btu/lb | Hi * 0.7 KJ/Kg | V2 m/s | V2 rel to CFC-113 |
|---|---|---|---|---|---|---|---|
| CFC-113 | 100 | | 10.92 | 7.6 | 17.8 | 133.3 | |
| PEIK plus (B): | | | 11.55 | 8.1 | 18.8 | 137.1 | 103% |
| HFC-263fa | 78.4 | 21.6 | 12.36 | 8.7 | 20.1 | 141.9 | 106% |
| HFC-272fa | 74.7 | 25.3 | 12.8 | 9.0 | 20.8 | 144.4 | 108% |
| HFC-365mfc | 50.0 | 50.0 | 12.62 | 8.8 | 20.5 | 143.3 | 108% |
| HFC-392p | 50.6 | 49.4 | 15.23 | 10.7 | 24.8 | 157.5 | 118% |
| HFC-392qe | 78.4 | 21.6 | 12.87 | 9.0 | 21.0 | 144.8 | 109% |
| HFC-392qfe | 84.9 | 15.1 | 12.5 | 8.8 | 20.4 | 142.7 | 107% |
| HFC-392qff | 92.5 | 7.5 | 12.12 | 8.5 | 19.7 | 140.5 | 105% |
| HFC-392qqz | 55.9 | 44.1 | 15.48 | 10.8 | 25.2 | 158.8 | 119% |
| HFC-392qy | 86.8 | 13.2 | 12.46 | 8.7 | 20.3 | 142.4 | 107% |
| HFC-392see | 75.0 | 25.0 | 13.18 | 9.2 | 21.5 | 146.5 | 110% |
| HFC-4-10-3m | 47.5 | 52.5 | 15.07 | 10.5 | 24.5 | 156.6 | 118% |
| HFC-4-10-3mfsz | 45.4 | 54.6 | 15.03 | 10.5 | 24.5 | 156.4 | 117% |
| HFC-4-11-2p | 95.2 | 4.8 | 12.04 | 8.4 | 19.6 | 140.0 | 105% |
| HFC-4-11-2qe | 90.1 | 9.9 | 12.33 | 8.6 | 20.1 | 141.7 | 106% |
| HFC-4-11-2sc | 82.0 | 18.0 | 13.17 | 9.2 | 21.4 | 146.4 | 110% |
| HFC-43-10mee | 73.6 | 26.4 | 11.59 | 8.1 | 18.9 | 137.4 | 103% |
| HFC-5-12-3m | 96.0 | 4.0 | 11.98 | 8.4 | 19.5 | 139.7 | 105% |
| HFC-C354cc | 73.2 | 26.8 | 12.56 | 8.8 | 20.5 | 143.0 | 107% |
| PFBE | 50.0 | 50.0 | 12.29 | 8.6 | 20.0 | 141.5 | 106% |

TABLE 7

| Refrigerant composition | wt % PEIK | wt % B | Evap Pres (Psia) | Evap Pres (kPa) | Cond Pres (Psia) | Cond Pres (kPa) | Compr Disch Temp (F.) | Compr Disch Temp (C.) | COP | Capacity (Btu/min) | Capacity (kW) |
|---|---|---|---|---|---|---|---|---|---|---|---|
| CFC-113 | | | 2.7 | 19 | 12.8 | 88 | 156.3 | 69.1 | 4.18 | 14.8 | 0.26 |
| PEIK plus B: | | | | | | | | | | | |
| HFC-263fa | 78.4 | 21.6 | 2.5 | 17 | 13.3 | 92 | 139.7 | 59.8 | 4.02 | 16.1 | 0.28 |
| HFC-272fa | 74.7 | 25.3 | 4.3 | 29 | 20.4 | 141 | 142.9 | 61.6 | 3.95 | 25.1 | 0.44 |
| HFC-365mfc | 50.0 | 50.0 | 2.9 | 20 | 14.5 | 100 | 135.2 | 57.3 | 3.96 | 17.5 | 0.31 |
| HFC-392p | 50.6 | 49.4 | 3.9 | 27 | 17.9 | 124 | 145.6 | 63.1 | 4.08 | 23.1 | 0.40 |
| HFC-392qe | 78.4 | 21.6 | 3.7 | 25 | 18.0 | 124 | 134.9 | 57.2 | 3.87 | 21.4 | 0.37 |

TABLE 7-continued

| Refrigerant composition | wt % PEIK | wt % B | Evap Pres (Psia) | Evap Pres (kPa) | Cond Pres (Psia) | Cond Pres (kPa) | Compr Disch Temp (F.) | Compr Disch Temp (C.) | COP | Capacity (Btu/min) | Capacity (kW) |
|---|---|---|---|---|---|---|---|---|---|---|---|
| HFC-392qfe | 84.9 | 15.1 | 3.1 | 21 | 15.7 | 108 | 132.2 | 55.7 | 3.86 | 18.3 | 0.32 |
| HFC-392qff | 92.5 | 7.5 | 2.5 | 17 | 13.4 | 93 | 128.7 | 53.7 | 3.81 | 15.1 | 0.26 |
| HFC-392qqz | 55.9 | 44.1 | 1.8 | 13 | 9.7 | 67 | 149.0 | 65.0 | 4.19 | 12.3 | 0.22 |
| HFC-392qy | 86.8 | 13.2 | 2.9 | 20 | 15.2 | 105 | 131.2 | 55.1 | 3.91 | 17.8 | 0.31 |
| HFC-392see | 75.0 | 25.0 | 3.8 | 26 | 18.7 | 129 | 137.5 | 58.6 | 3.81 | 21.8 | 0.38 |
| HFC-4-10-3m | 47.5 | 52.5 | 4.1 | 28 | 18.8 | 130 | 134.3 | 56.8 | 3.92 | 23.1 | 0.40 |
| HFC-4-10-3mfsz | 45.4 | 54.6 | 4.3 | 29 | 19.3 | 133 | 134.3 | 56.8 | 3.93 | 23.9 | 0.42 |
| HFC-4-11-2p | 95.2 | 4.8 | 2.1 | 15 | 11.9 | 82 | 126.9 | 52.7 | 3.81 | 13.1 | 0.23 |
| HFC-4-11-2qe | 90.1 | 9.9 | 2.6 | 18 | 14.0 | 96 | 127.8 | 53.2 | 3.79 | 15.6 | 0.27 |
| HFC-4-11-2sc | 82.0 | 18.0 | 2.7 | 18 | 13.8 | 95 | 129.8 | 54.3 | 3.86 | 16.0 | 0.28 |
| HFC-43-10mee | 73.6 | 26.4 | 2.5 | 17 | 13.3 | 92 | 126.0 | 52.2 | 3.77 | 14.7 | 0.26 |
| HFC-5-12-3m | 96.0 | 4.0 | 2.1 | 14 | 11.8 | 81 | 125.8 | 52.1 | 3.78 | 12.8 | 0.22 |
| HFC-C354cc | 73.2 | 26.8 | 2.3 | 16 | 12.2 | 84 | 134.6 | 57.0 | 3.96 | 14.5 | 0.25 |
| PFBE | 50.0 | 50.0 | 1.7 | 12 | 9.8 | 67 | 128.3 | 53.5 | 3.86 | 10.9 | 0.19 |

Data show the compositions of the present invention have evaporator and condenser pressures similar to CFC-113. Some compositions also have higher capacity or energy efficiency (COP) than CFC-113.

What is claimed is:

1. A azeotropic or azeotropic-like composition wherein the composition comprises:
    about 1 to about 99 weight percent 1,1,1,2,2,4,5,5,5-nonafluoro-4-(trifluoromethyl)-3-pentanone and about 99 to about 1 weight percent 1,1,2,2-tetrafluorocyclobutane.

2. A composition as in claim 1 wherein the composition is an azeotropic comprising
    73.2 weight percent 1,1,1,2,2,4,5,5,5-nonafluoro-4-(trifluoromethyl)-3-pentanone and 26.8 weight percent 1,1,2,2-tetrafluorocyclobutane having a vapor pressure of about 14.7 psia (101 kPa) at a temperature of about 48.7° C.

3. A process for producing refrigeration, said process comprising evaporating the refrigerant composition of claim 1 in the vicinity of a body to be cooled, and thereafter condensing said composition.

4. A method as in claim 3 wherein the refrigerant composition further comprises at least one ultra-violet fluorescent dye selected from the group consisting of naphthalimides, perylenes, coumarins, anthracenes, phenanthracenes, xanthenes, thioxanthenes, naphthoxanthenes, fluoresceins, derivatives of said dye and combinations thereof.

5. A process for producing heat, said process comprising condensing the heat transfer composition of claim 1 in the vicinity of a body to be heated, and thereafter evaporating said composition.

6. A method as in claim 5 wherein the heat transfer composition further comprises at least one ultra-violet fluorescent dye selected from the group consisting of naphthalimides, perylenes, coumarins, anthracenes, phenanthracenes, xanthenes, thioxanthenes, naphthoxanthenes, fluoresceins, derivatives of said dye and combinations thereof.

7. A process for transferring heat, said process comprising transferring the composition of claim 1 from the vicinity of a heat source to a heat sink.

8. The composition of claim 1, further comprising at least one ultra-violet fluorescent dye selected from the group consisting of naphthalimides, perylenes, coumarins, anthracenes, phenanthracenes, xanthenes, thioxanthenes, naphthoxanthenes, fluoresceins, derivatives of said dye and combinations thereof.

9. The composition of claim 8, further comprising at least one solubilizing agent selected from the group consisting of hydrocarbons, dimethylether, polyoxyalkylene glycol ethers, amides, ketones, nitriles, chlorocarbons, esters, lactones, aryl ethers, hydrofluoroethers, and 1,1,1-trifluoroalkanes; and wherein the refrigerant and solubilizing agent are not the same compound.

10. The composition of claim 9, wherein said solubilizing agent is selected from the group consisting of:
    a) polyoxyalkylene glycol ethers represented by the formula $R^1[(OR^2)_xOR^3]_y$, wherein: x is an integer from 1 to 3; y is an integer from 1 to 4; $R^1$ is selected from hydrogen and aliphatic hydrocarbon radicals having 1 to 6 carbon atoms and y bonding sites; $R^2$ is selected from aliphatic hydrocarbylene radicals having from 2 to 4 carbon atoms; $R^3$ is selected from hydrogen, and aliphatic and alicyclic hydrocarbon radicals having from 1 to 6 carbon atoms; at least one of $R^1$ and $R^3$ is selected from said hydrocarbon radicals; and wherein said polyoxyalkylene glycol ethers have a molecular weight of from about 100 to about 300 atomic mass units;
    b) amides represented by the formulae $R^1CONR^2R^3$ and cyclo-[$R^4CON(R^5)$—], wherein $R^1$, $R^2$, $R^3$ and $R^5$ are independently selected from aliphatic and alicyclic hydrocarbon radicals having from 1 to 12 carbon atoms, and at most one aromatic radical having from 6 to 12 carbon atoms; $R^4$ is selected from aliphatic hydrocarbylene radicals having from 3 to 12 carbon atoms; and wherein said amides have a molecular weight of from about 100 to about 300 atomic mass units;
    c) ketones represented by the formula $R^1COR^2$, wherein $R^1$ and $R^2$ are independently selected from aliphatic, alicyclic and aryl hydrocarbon radicals having from 1 to 12 carbon atoms, and wherein said ketones have a molecular weight of from about 70 to about 300 atomic mass units;
    d) nitriles represented by the formula $R^1CN$, wherein $R^1$ is selected from aliphatic, alicyclic or aryl hydrocarbon radicals having from 5 to 12 carbon atoms, and wherein said nitriles have a molecular weight of from about 90 to about 200 atomic mass units;

e) chlorocarbons represented by the formula $RCl_x$, wherein; x is selected from the integers 1 or 2; R is selected from aliphatic and alicyclic hydrocarbon radicals having from 1 to 12 carbon atoms; and wherein said chlorocarbons have a molecular weight of from about 100 to about 200 atomic mass units;

f) aryl ethers represented by the formula $R^1OR^2$, wherein: $R^1$ is selected from aryl hydrocarbon radicals having from 6 to 12 carbon atoms; $R^2$ is selected from aliphatic hydrocarbon radicals having from 1 to 4 carbon atoms; and wherein said aryl ethers have a molecular weight of from about 100 to about 150 atomic mass units;

g) 1,1,1-trifluoroalkanes represented by the formula $CF_3R^1$, wherein $R^1$ is selected from aliphatic and alicyclic hydrocarbon radicals having from about 5 to about 15 carbon atoms;

i) fluoroethers represented by the formula $R^1OCF_2CF_2H$, wherein $R^1$ is selected from aliphatic and alicyclic hydrocarbon radicals having from about 5 to about 15 carbon atoms; or wherein said fluoroethers are derived from fluoro-olefins and polyols, wherein said fluoro-olefins are of the type $CF_2=CXY$, wherein X is hydrogen, chlorine or fluorine, and Y is chlorine, fluorine, $CF_3$ or $OR_f$, wherein $R_f$ is $CF_3$, $C_2F_5$, or $C_3F_7$; and said polyols are of the type $HOCH_2CRR'(CH_2)_z(CHOH)_xCH_2(CH_2OH)_y$, wherein R and R' are hydrogen, $CH_3$ or $C_2H_5$, x is an integer from 0-4, y is an integer from 0-3 and z is either zero or 1; and j) lactones represented by structures [B], [C], and [D]:

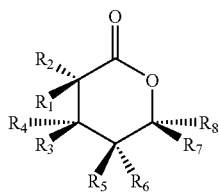
[B]

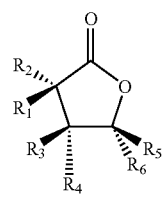
[C]

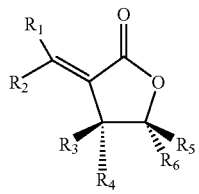
[D]

wherein, $R_1$ through $R_8$ are independently selected from hydrogen, linear, branched, cyclic, bicyclic, saturated and unsaturated hydrocarbyl radicals; and the molecular weight is from about 100 to about 300 atomic mass units; and k) esters represented by the general formula $R^1CO_2R^2$, wherein $R^1$ and $R^2$ are independently selected from linear and cyclic, saturated and unsaturated, alkyl and aryl radicals; and wherein said esters have a molecular weight of from about 80 to about 550 atomic mass units.

11. A process for detecting a leak at or in the vicinity of a refrigeration or air conditioning apparatus, said process comprising: providing a composition of claim 8 into said apparatus, and providing a suitable means for detecting said composition at a leak point or in the vicinity of said apparatus.

12. A method as in claim 4, wherein the refrigerant composition further comprises at least one solubilizing agent selected from the group consisting of hydrocarbons, dimethylether, polyoxyalkylene glycol ethers, amides, ketones, nitriles, chlorocarbons, esters, lactones, aryl ethers, hydrofluoroethers, and 1,1,1-trifluoroalkanes; and wherein the refrigerant and solubilizing agent are not the same compound.

13. A method as in claim 12 wherein the composition is introduced into a compression refrigeration or air conditioning apparatus by (i) dissolving the ultraviolet fluorescent dye in the refrigerant composition or heat transfer fluid in the presence of the solubilizing agent, and introducing the combination into said compression refrigeration or air conditioning apparatus or (ii), combining solubilizing agent and UV fluorescent dye and introducing said combination into said compression refrigeration or air conditioning apparatus containing refrigerant and/or heat transfer fluid.

14. The composition of claim 1 further comprising a stabilizer, water scavenger, or odor masking agent.

15. The composition of claim 14 wherein said stabilizer is selected from the group consisting of nitromethane, hindered phenols, hydroxylamines, thiols, phosphites and lactones.

16. The composition of claim 14 wherein said water scavenger is an ortho ester.

* * * * *